US006592612B1

(12) United States Patent
Samson et al.

(10) Patent No.: US 6,592,612 B1
(45) Date of Patent: Jul. 15, 2003

(54) METHOD AND APPARATUS FOR PROVIDING HEAT EXCHANGE WITHIN A CATHETER BODY

(75) Inventors: Wilfred Samson, Saratoga, CA (US); Hoa Nguyen, San Jose, CA (US); Mike Lee, San Francisco, CA (US); Brady Esch, San Jose, CA (US); Eric Olsen, Los Gatos, CA (US); Jeff Valko, San Clemente, CA (US)

(73) Assignee: Cardeon Corporation, Cupertino, CA (US)

( * ) Notice: Subject to any disclaimer, the term of this patent is extended or adjusted under 35 U.S.C. 154(b) by 0 days.

(21) Appl. No.: 09/564,958

(22) Filed: May 4, 2000

(51) Int. Cl.$^7$ .................................................. A61F 7/00
(52) U.S. Cl. ...................... 607/105; 606/28; 604/113
(58) Field of Search ..................... 604/49, 113, 114; 607/96, 101–107, 113, 116; 606/27–29

(56) References Cited

U.S. PATENT DOCUMENTS

| | | | |
|---|---|---|---|
| 4,483,341 A | | 11/1984 | Witteles |
| 4,625,712 A | | 12/1986 | Wampler |
| 4,860,744 A | | 8/1989 | Johnson et al. |
| 4,919,647 A | | 4/1990 | Nash |
| 4,944,722 A | | 7/1990 | Carriker et al. |
| 4,969,865 A | | 11/1990 | Hwang et al. |
| 5,222,938 A | * | 6/1993 | Behl ............................ 604/49 |
| 5,275,595 A | | 1/1994 | Dobak, III |
| 5,308,320 A | | 5/1994 | Safar et al. |
| 5,337,572 A | | 8/1994 | Longsworth |
| 5,368,555 A | | 11/1994 | Sussman et al. |
| 5,368,591 A | * | 11/1994 | Lennox et al. ................ 606/27 |
| 5,507,629 A | | 4/1996 | Jarvik |
| 5,578,008 A | | 11/1996 | Hara |
| 5,794,629 A | | 8/1998 | Frazee |
| 5,837,003 A | * | 11/1998 | Ginsburg .................... 607/106 |
| 5,879,329 A | | 3/1999 | Ginsburg |

(List continued on next page.)

FOREIGN PATENT DOCUMENTS

| | | |
|---|---|---|
| WO | WO 92/13243 | 8/1992 |
| WO | WO 92/00204 | 1/1999 |
| WO | WO 99/59652 | 11/1999 |

OTHER PUBLICATIONS

Gravelee, et al, Cardiopulmonary Bypass Principles and Practice, 1993.
David P. Bichell, MD, et al., Axilloaxillary Cardiopulmonary Bypass: A Practical Alternative to Femorofemoral Bypass. © 1997 by The Society of Thoracic Surgeons Published by Elsevier Science Inc., pp. 702–705.
Joseph F. Sabik, MD, et al., Axillary Artery: An Alternative Site of Arterial Cannulation for Patients with Extensive Aortic and Peripheral Vacscular Disease, © 1995 by Mosby–Year Book, Inc., The Journal of Thoracic and Cardiovascular Surgery , pp. 886–891.
Nicholas T. Kouchoukos, et al., Perfusion for Thoracic Aortic Surgery, Section V. Clinical Application and Management of CPB, pp. 636–654.

*Primary Examiner*—Roy D. Gibson
(74) *Attorney, Agent, or Firm*—Fulwider Patton Lee & Utecht, LLP

(57) ABSTRACT

The present invention relates to catheters for selectively cooling or warming tissue within a patient's vasculature. The present invention utilizes novel heat exchanging devices, which reside inside the catheter body for selectively altering the temperature of fluid that flows through the catheter shaft. In addition, the present invention utilizes novel pumping devices, which reside within a patient's vasculature for withdrawing oxygenated blood into the catheter body where heat exchange occurs across a heat transfer interface for selective cooling or warming of the blood occurs. The present invention can be used in a multiplicity of medical disciplines where it is advantageous to selectively alter the temperature of tissue, including beating heart applications, as well as stopped heart medical interventions.

31 Claims, 11 Drawing Sheets

U.S. PATENT DOCUMENTS

| | | |
|---|---|---|
| 5,901,783 A | 5/1999 | Dobak, III et al. |
| 5,908,407 A | 6/1999 | Frazee et al. |
| 5,911,685 A | 6/1999 | Siess et al. |
| 5,957,963 A | 9/1999 | Dobak, III |
| 5,971,979 A | 10/1999 | Joye et al. |
| 5,981,863 A | 11/1999 | Yamashita et al. |
| 5,997,816 A | 12/1999 | McIntosh et al. |
| 6,019,783 A | 2/2000 | Philips et al. |
| 6,033,383 A * | 3/2000 | Ginsburg .................... 604/113 |
| 6,126,684 A * | 10/2000 | Gobin et al. ................ 607/113 |
| 6,146,411 A * | 11/2000 | Noda et al. ................. 607/105 |
| 6,231,594 B1 * | 5/2001 | Dae ............................. 607/96 |
| 6,264,679 B1 * | 7/2001 | Keller et al. .................. 606/21 |
| 6,299,599 B1 * | 10/2001 | Pham et al. ................ 604/113 |
| 6,368,304 B1 * | 4/2002 | Aliberto et al. ........ 604/101.05 |
| 6,409,747 B1 * | 6/2002 | Gobin et al. ................ 604/113 |

\* cited by examiner

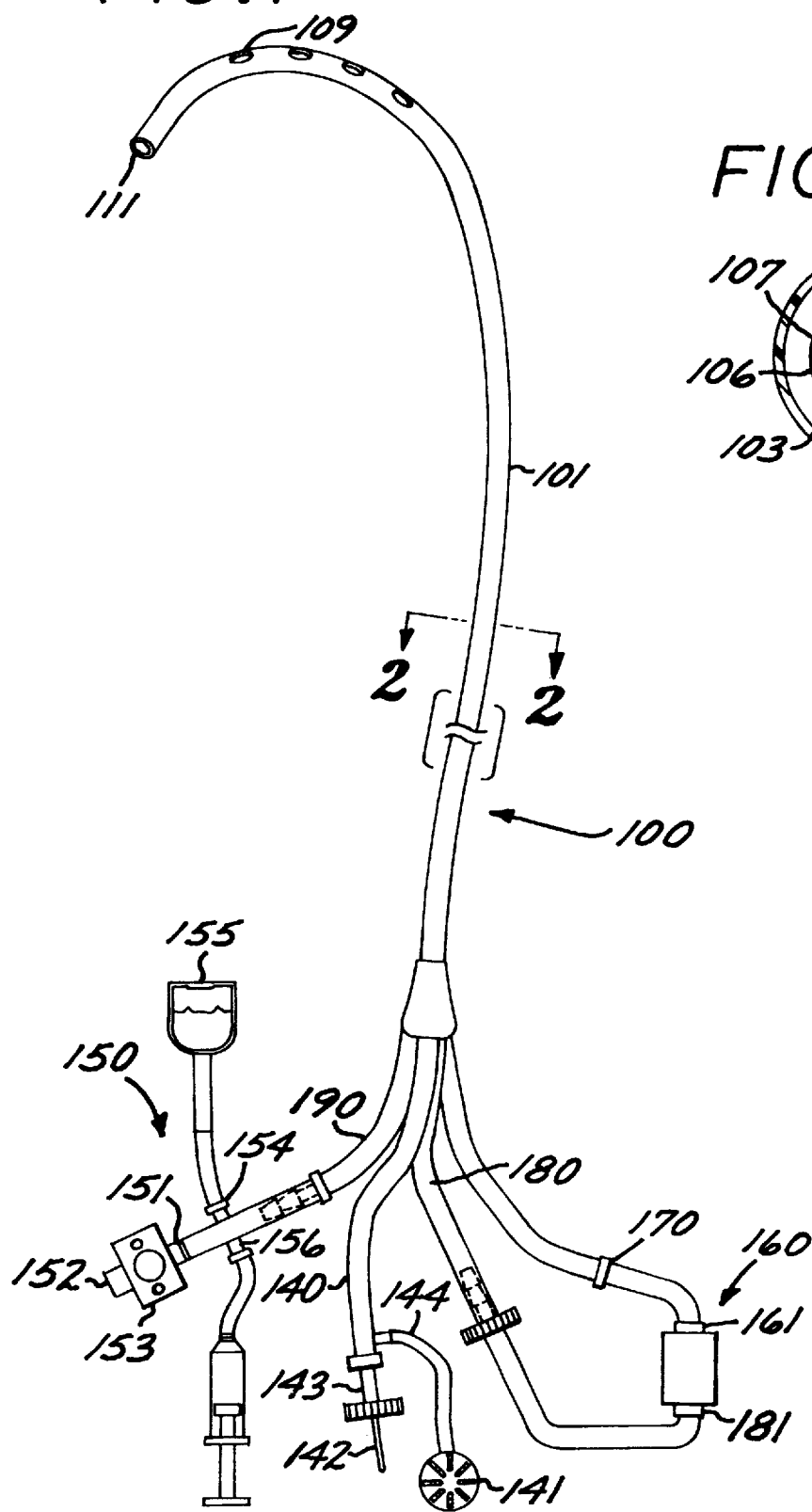
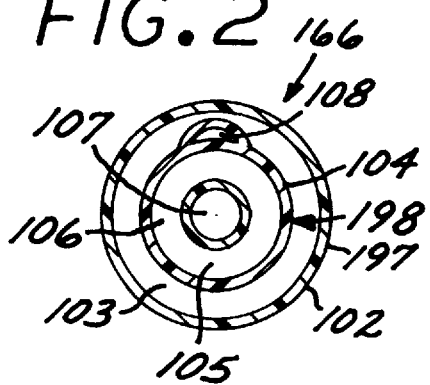

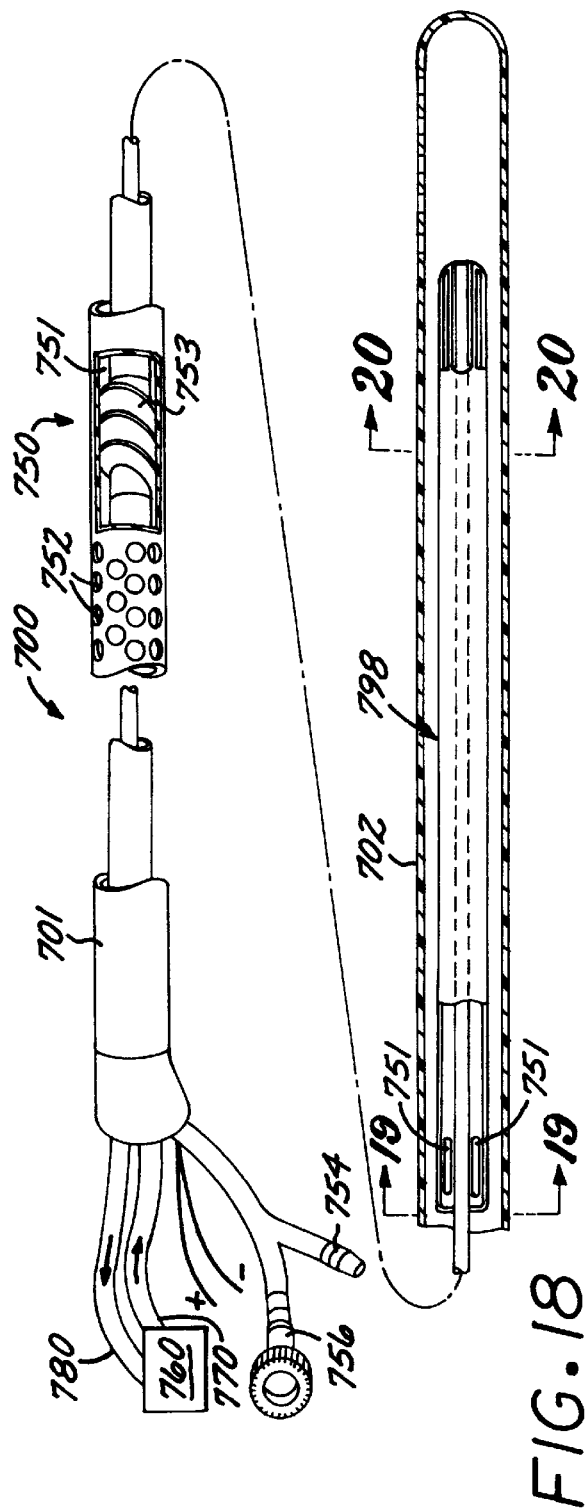
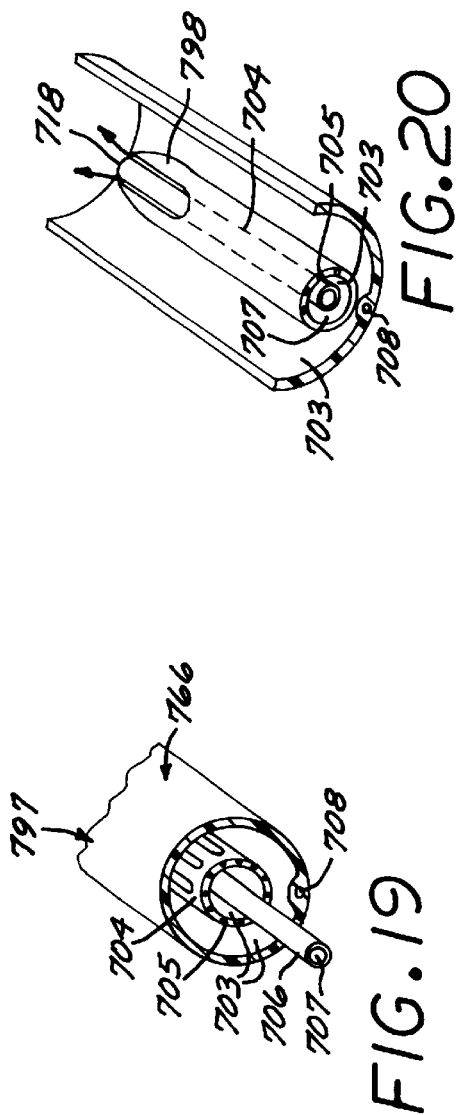
FIG. 18
FIG. 19
FIG. 20

METHOD AND APPARATUS FOR PROVIDING HEAT EXCHANGE WITHIN A CATHETER BODY

BACKGROUND OF THE INVENTION

1. Field of the Invention

The present invention relates to catheters or cannulae to be used during medical procedures where it is desirable to create a cool or warm environment selectively and more specifically to protect the brain. Hypothermia has been suggested as one of the most potent approaches to both minimizing and therapeutically treating ischemic brain injury. Over the past decade there has been an increased interest in the use of hypothermia as a means for creating a neuroprotective environment during cardiac, cerebrovascular and neurologic surgery, as well as for acute stroke therapy and traumatic head injury. Although not all of the etiological mechanisms are fully understood, hypothermia confers a neuroprotective environment by (1) reducing cerebral metabolism, making the brain more tolerant of reduced blood flow; (2) decreasing excitatory amino acids; (3) stabilizing the blood brain barrier and (4) decreasing heat shock proteins after induced brain injury.

Even though the benefits of cerebral hypothermia have been documented, the widespread use in surgery, neurosurgery, trauma, closed head injury and stroke has not been readily adopted. This lack of adoption is based in large part because of the complications associated with the systemic nature of achieving the hypothermic condition. For example, in cardiac surgery perfusing the entire patient with hypothermic blood from an extracorporeal bypass unit is the common method for obtaining cerebral hypothermia. Using external heat exchangers such as those described in U.S. Pat. No. 5,997,816 to McIntosh et al. and U.S. Pat. No. 5,421,405 to Goddin et al., the teachings of which are hereby incorporated by reference, total body hypothermia can be induced. This modality of hypothermia carries potential risks, including arrhythmias, infection and coagulopathies. To avoid these complications, there has been a trend toward performing cardiopulmonary bypass at normothermic temperatures and using hypothermia in a very selective group of procedures including aortic arch dissections and heart lung transplantation. In addition, topical cooling in the form of ice baths, cooling helmets and cooling blankets have been proposed for cooling the patient's brain in cases of severe head trauma and stroke, however these technologies are inefficient and take too long to be truly effective for rapid cooling of the brain core.

Therefore, what has been needed and heretofore unavailable, is a method and apparatus for selectively cooling the brain apart from the rest of the body in any medical procedure where an ischemic event may or has occurred. By employing novel pumping and cooling devices that require minimal priming volume, along with new methods for controlling patient temperature selectively, the shortcomings of previous medical devices can be overcome. Such methods and devices would offer clinicians significant advantages in managing patients at high risk of neurologic damage, thereby improving outcomes. Furthermore, selective cerebral hypothermic therapy can be used in beating heart cardiac surgery, minimally invasive cardiac surgery, open chest heart surgery, traumatic brain injury, neurosurgery and stroke. The methods and apparatus can be used to extend the therapeutic window for other interventions, can enhance the effects of pharmacological and other co-therapies, as well as provide a neuroprotective environment for aneurysm clipping, coil delivery and other forms of interventional neurology and cardiac surgery.

2. Description of the Background Art

U.S. Pat. No. 5,971,979 to Joye et al. describes a method of delivering compressed cryogenic fluid to the interior of a balloon catheter for selectively freezing a patient's vasculature. U.S. Pat. No. 6,019,783 to Philips, U.S. Pat. No. 4,860,744 to Johnson et al. and U.S. Pat. No. 4,483,341 to Witteles describe thermoelectric cooling systems. U.S. Pat. No. 5,901,783 to Dobak, III describes a cryogenic heat exchanger. U.S. Pat. No. 5,275,595 also to Dobak, III describes a closed cycle cryosurgical instrument. U.S. Pat. No. 5,957,963 to Dobak, III describes a method and apparatus for selective organ hypothermia. U.S. Pat. No. 8,837,003 to Ginsburg describes a method and apparatus for controlling a patient's body temperature by in situ cooling of blood. U.S. Pat. No. 5,794,629 and 5,908,407 to Frazee contemplate the use of catheters for delivering blood flow to selective organs by retrograde perfusion. U.S. Pat. No. 5,820,593 and 5,906,588 to Safar et al. describe methods and apparatus for selectively cooling body organs. Cryogenic fluid sources are described in U.S. Pat. No. 5,644,502 to Little and micropumps are disclosed in U.S. Pat. No. 4,919,647 to Nash, U.S. Pat. No. 5,911,685 to Siess et al., U.S. Pat. No. 5,507,629 to Jarvik, U.S. Pat. No. 4,625,712 and 5,695,471 to Wampler, WO 99/02204 to Aboul-Hosn and WO 99/59652 to Aboul-Hosn. The full disclosures of each of the above US patents are hereby incorporated by reference in their entirety.

SUMMARY OF THE INVENTION

In keeping with the foregoing discussion, the present invention provides novel cooling and perfusion devices, which can be used in a variety of medical procedures, including, but not limited to: stroke, closed head brain injury, trauma, rescusitation, and all forms of general surgery and cardiac surgery. The methods and devices of the present invention include in-line heat exchangers as well as in-line intravascular blood pumps, which reduce priming volume and are compact in design.

In one illustrative embodiment, the present invention provides a fluid transport system, a flexible elongate catheter, and a temperature regulation assembly. The catheter is comprised of three tubular bodies/members, which extend in a substantially coaxial configuration. The tubular members are collectively referred to as a shaft assembly and may be manufactured from metals, alloys, flexible thermoplastic materials, thermoplastic elastomers or thermoset elastomers. More specifically, suitable materials for the shaft assembly include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the shaft assembly or any one of the tubular members may be made of thin walled metallic tubing or hypotube constructed of materials such as stainless steel, platinum, titanium, nitinol alloys and Cobalt alloys such as Elgiloy and Carpenter MP 35.

The innermost tubular member has a delivery lumen that is sized and configured to deliver a heat exchanging medium. There are a variety of heat exchanging mediums that are well known in the art including, but not limited to: water, blood, saline and compressed refrigerants, such as freon, liquid nitrogen or nitrous oxide. A second tubular member has a second lumen/return lumen that is sized and configured to serve as a return for the heat exchanging medium. The first tubular member and the second tubular member together comprise a heat exchanging apparatus that extends at least in part through the outermost tubular member/third tubular member. The outermost tubular member serves as a housing for the heat exchanging apparatus and has an internal lumen/fluid lumen which serves as a fluid lumen. The fluid lumen is isolated from the return lumen creating a heat exchanging interface that facilitates heat exchange between the fluid lumen and the return lumen. Fluid such as blood, water, saline, lysing agents, clot dissolving pharmacological agents, glutamate antagonists, calcium channel blockers, salt based solutions or any other fluid composition or combination may travel over the surface of the second tubular member through the fluid lumen where temperature can be controlled and heat transfer occurs.

A guidewire lumen is also provided to facilitate the insertion of a steerable guidewire. In alternative embodiments, the guidewire lumen may be incorporated into one of the other lumens to create a more compact design, or a fixed guidewire may be attached to the distal end of the catheter shaft, as is well known in the art. Furthermore, the guidewire lumen can serve to facilitate the insertion of other medical devices or microcatheters such as carotid stent catheters, aneurysm clip catheters, dilation catheters, diagnostic catheters, coil catheters, aneurysm catheters or occlusion catheters which access the patient's vasculature through perfusion ports or a specific access port designated along the length of the catheter shaft, which is sized and configured for optimal access, or out the distal opening.

The innermost tubular member may have a plurality of outputs representing expansion orifices that are located along the length of the shaft. The expansion orifices are sized and configured for allowing the expansion of the heat transfer material into the lower pressure region of the second tubular member. The outputs may be created by mechanically penetrating the surface of the hypotube, or alternatively may be formed by using lasers or by chemical etching. Preferably, the spacing between the orifices, as well as the size and shape are selected to allow for the appropriate expansion of the heat exchanging medium to provide the appropriate temperature regulation under certain pressure conditions. In one preferred embodiment, the spacing between the orifices is selected such that uniform cooling along the length of the shaft is possible. The outputs may be located directly across from one another or alternatively may be staggered along the length of the first tubular member.

In one illustrative embodiment, compressed nitrous oxide is delivered through the delivery lumen where expansion occurs upon exiting the outputs. The nitrous oxide vaporizes as it expands, cooling the second tubular member to facilitate heat transfer as blood or other fluid flows over the cold surface.

Alternatively, or in addition thereto, the distal end of the inner tubular member may also be configured to have an integral heat transfer bellows. In addition, or alternatively the distal end of the inner tubular member may be coupled to a Joule-Thomson valve. Furthermore, only one distal output with or without the aforementioned heat transfer bellows or Joule-Thomson valve may be necessary to accomplish desired results.

In another illustrative embodiment cold or warm water may be used as the heat exchanging medium. A closed circulation system can be maintained by circulating the water through the catheter by maintaining a higher pressure on the input of the inner tube and a lower pressure on the output of the second tubular member to create the desired flow of heat exchanging medium through the heat transfer system.

The second tubular member can be formed from a variety of materials as discussed above and in a preferred embodiment a high thermal conductivity metal is used to enhance optimum heat transfer between the surface of the second inner tube and fluid communicating within the fluid lumen of the outer tubular member. Examples of materials having high thermal conductivity include copper, gold, nitinol, platinum iridium, aluminium and stainless steel. In addition, the above listed materials may be coated to ensure hemocompatibility. Furthermore, the second tubular member may be constructed to have fins or other means for enhancing the surface area and corresponding heat transfer ability of the second tubular member. For example, in one preferred embodiment the second tubular member may be constructed of a substantially cylindrical tube having a plurality of substantially parallel longitudinal corrugations. Each corrugation increases the total amount of surface area capable of heat transfer. Blood or other fluid flows over the surface of the exterior fluid flow channel and the heat exchanging medium is circulated through the interior return channels.

A first tube fitting is connected by known means to the output of a temperature regulation assembly for delivering the heat exchange material to the delivery lumen. A second tube fitting is connected by known means to the input of the temperature regulation assembly serving as a return for the heat exchange material to the temperature regulation assembly. In an alternative embodiment, the return lumen may open to atmosphere or to a separate holding chamber, rather than being recirculated through the temperature regulation assembly, as would be typical in a closed cycle.

A fluid transport system has an input and an output in fluid communication with the fluid lumen of the catheter. An external pump is coupled to a tube fitting where fluid can be communicated from the patient's peripheral artery or vein. The term external pump is intended to describe generically all pumps that reside outside of the vasculature of the human body. External pumps may be in the form of centrifugal pumps, peristaltic pumps or roller pumps, as are commonly associated with cardiopulmonary bypass machines. In addition, mechanical hand pumps that are operated through manual pumping mechanisms, incremental squeeze pumps, diaphragm pumps or displacement pumps for emergency resuscitation or trauma can be used. In alternative embodiments, micropumps or axial pumps can be used which are located within the catheter body or within the tubing circuit, but outside of the patient's vasculature, thereby reducing priming volume. Alternatively, in another illustrative embodiment internal pump(s) can be used. The term internal pump is meant to describe generically pumps with impellers or auger type pumps that reside within a patient's vasculature. The fluid transportation system has a first luer connector connected to a fluid composition altering source and a second luer connector or other suitable fitting capable of fluid sampling or for monitoring pressure, temperature or chemical composition.

A fourth tube connector is in fluid communication with the guidewire lumen having a hemostasis valve, a Touhy-Borst fitting or other suitable fitting capable of facilitating the insertion of guidewire(s) or other medical instruments through the guidewire lumen.

Another embodiment of the present invention, configured for selectively cooling tissue, comprises a catheter, a fluid transport system and a temperature regulation assembly. The catheter shaft is comprised of a delivery lumen that is sized and configured to deliver a heat exchanging medium at least in part through the length of the catheter shaft. A return lumen is sized and configured to serve as a return for the heat exchanging medium. The delivery lumen and the return lumen together serve as a heat exchanging apparatus that extends at least in part through the catheter shaft. The catheter shaft serves as a housing for the heat exchanging apparatus allowing for the selective cooling or heating of a fluid within a catheter body. The fluid transport system has an internal pump connected to a power lead extending through the catheter shaft to a remote power source. In alternative embodiments, a separate lumen may be provided to house the power lead or alternatively the power lead may be integrally formed within the catheter shaft where no separate lumen is required. Alternatively, the power source may reside adjacent to the internal pump using battery power or the like where no power lead is necessary.

The internal pump communicates autologous blood from a vessel to a fluid lumen where the blood travels over the surface of the heat exchanging interface to cool or warm the blood. Fluid such as blood, in addition to other additives such as thrombolytics, lysing agents, clot dissolving pharmacological agents, glutamate antagonists, calcium channel blockers, salt based solutions or any other fluid composition or combination will travel over the surface where temperature can be controlled and heat transfer occurs.

A guidewire lumen is also provided to facilitate the insertion of a steerable guidewire. In alternative embodiments the guidewire lumen may be incorporated into one of the other lumens to create a more compact design where a fixed guidewire may be attached to the distal end of the catheter shaft, as is well known in the art. Furthermore, the guidewire lumen can serve to facilitate the insertion of other medical devices or microcatheters, such as carotid stent catheters, aneurysm clip catheters, dilation catheters, diagnostic catheters, coil catheters or occlusion catheters which access the patient's vasculature through perfusion ports or a specific access port designated along the length of the catheter shaft, which is sized and configured for optimal access, or out the distal opening where the device is mechanically similar to a guide catheter.

A manifold is attached to the catheter shaft and has fittings coupled to the various lumens of the catheter shaft. A fitting is connected by known means to the output of a temperature regulation assembly for circulating the heat exchange material to the delivery lumen. A compressed refrigerant such as liquid nitrogen or nitrous oxide is used to deliver the heat exchange material to the delivery lumen. In another illustrative embodiment cold water is used. A second fitting is connected by known means to the input of the temperature regulation assembly as a return for the heat exchange material to the temperature regulation assembly. In alternative embodiments the return lumen may open to atmosphere or to a separate holding chamber rather than being recirculated through the temperature regulation assembly, as would be typical in a closed cycle circuit.

A hemostasis valve, Touhy-Borst fitting or other suitable fitting capable of facilitating insertion of other medical devices or instruments is in fluid communication with the guidewire lumen. Furthermore, a luer connector extending from the Touhy-Borst fitting is configured for measuring flow, pressure, temperature and chemical composition by way of ports or the end opening.

The catheter system of the present invention is multifunctional and is adapted to perform effectively in a variety of medical situations. For example, in an emergency situation, such as stroke, trauma, resuscitation or traumatic brain injury the catheter is designed for ease of insertion into a peripheral vessel for rapid cooling of the brain or warming the body or a combination of both. Alternatively, during an elective cardiac surgery including traditional stopped heart, beating heart or minimally invasive cardiac surgery or neurosurgery the catheter is effective for rapid cooling of the brain to create a cerebral protective environment. Methods for introducing the catheter include percutaneous insertion, arterial cutdown, Seldinger technique over a guidewire, as well as an aortotomy with a purse string suture. The catheter can be introduced through any peripheral access vessel including the subclavian, radial, iliac, femoral or brachial artery or alternatively through an intercostal space, median sternotomy minithoracotomy or left thoracotomy. Once inserted, the catheter is navigated into an operative position until blood perfusion ports are proximate or adjacent to the arch vessels. The brain is cooled selectively from the rest of the body rapidly and efficiently, as the internal pump directs blood over the heat exchanging interface where it is cooled along the length of the catheter shaft. The blood is cooled to the optimal temperature and exits out the perfusion ports where cooled fluid is delivered to the cerebral circulation in an efficient manner.

In embodiments where the catheter is navigated into the operative position over a guidewire and additional intervention is necessary, the guidewire is removed through a Touhy-Borst fitting and another medical instrument or device is inserted therethrough. In one preferred embodiment a carotid stent catheter is employed having an additional guidewire fitting and inflation fitting. The medical device may access any number of organs or vessels and therefore any number of ports may be implemented to facilitate the desired procedure. For example, if the heart is the target organ the end port may be the optimal port to reach the heart in peripheral approaches. Alternatively, if the cerebral vasculature or carotid arteries are the target area then side ports, which also serve as perfusion ports, might be the most desirable port(s) to use. In addition, in other alternative embodiments another port and or lumen designed especially for other medical devices can be implemented. Other medical devices which may be inserted through the catheter include angioplasty balloon catheters, stent catheters, atherectomy catheters, transmyocardial revascularization catheters, pigtail catheters, filters, in stent restenosis removal catheters, stent removal catheters, diagnostic catheters, angiogram catheters, carotid stent catheters, aneurysm clip catheters, coil delivery catheters, embolization therapy catheters, drug delivery catheters or secondary temperature regulation or measuring catheters or any other medical device.

In another embodiment of the present invention, an aortic isolator in the form of an expandable membrane or filter mesh is coupled to the distal portion of the catheter shaft. The expandable membrane is configured to have a top surface, a bottom surface, a proximal portion, a distal portion, a length and a width. The expandable membrane may be formed in a variety of configurations, however, in general, the expandable membrane will have an undeployed or collapsed state and a deployed or expanded state. In the collapsed state the expandable membrane is not substantially larger than the external diameter of the catheter shaft. In the expanded state, the membrane is configured to create two fluid flow paths, which optimize the cooling of the cerebral circulation. The expandable membrane may be deployed from an exterior surface of the catheter shaft, or it may be deployed from within a lumen in the catheter shaft or another catheter.

The expandable membrane has one or more biasing ribs or inflatable chambers, which serve a multiplicity of functions. In one preferred embodiment the inflatable chambers are in fluid communication with the delivery lumen of the heat exchanging apparatus. The heat exchanging medium is allowed to expand within the inflatable chambers, actuating the expandable membrane as well as cooling the inflatable membrane such that any blood residing within or flowing through the vessel that interfaces with the inflatable membrane becomes cooled. In a preferred embodiment, only the upper surface of the expandable membrane serves as a heat exchanging interface, that is, the surface facing toward the arch vessels is configured for cooling blood within the vessel. Blood traveling downstream which interfaces with the lower surface of the expandable membrane is kept normothermic by thermally insulating the lower surface of the membrane to prevent systemic cooling.

In another illustrative embodiment of the present invention the catheter shaft is deployed within a patient's aorta having an occluding member located near the distal end of the catheter shaft for stabilizing the catheter in an operative position. In addition, the catheter is configured for delivering a treated fluid to the cerebral circulation and can selectively cool cerebral tissue through an internal heat exchanger having an internal impeller pump.

BRIEF DESCRIPTION OF THE DRAWINGS

FIG. 1 is a side view of a first embodiment of the present invention comprising a catheter connected to a fluid transport system and temperature regulation assembly.

FIG. 2 is a magnified lateral cross section of the catheter of FIG. 1 taken along line 2—2.

FIG. 18 is a seventh embodiment of the present invention having a heat transfer interface configured to cool or warm blood on an interior surface and an exterior surface of the heat transfer interface.

FIG. 19 is a perspective cross-sectional view illustrating the heat exchanging apparatus as it extends within the catheter body.

FIG. 20 is a cutaway perspective view illustrating the distal end and expansion orifice of the heat exchanging apparatus.

DETAILED DESCRIPTION OF THE INVENTION

The present invention provides a flexible elongated catheter having a fluid lumen and an internal heat exchanger extending at least in part within the fluid lumen of the catheter body. The heat exchanger has sufficient surface area in contact with fluid residing within or communicated through the fluid lumen such that heat transfer is accomplished within the catheter. Although the present invention is described predominately for the purpose of cooling brain tissue, it will be understood by one of ordinary skill in the art that the device and methods of the present invention can be modified to adjust the temperature of any body tissue, either by warming or cooling. In addition, the embodiments of the present invention are directed toward arterial access and perfusion, however it is to be understood that perfusion of tissue can also be accomplished through the venous system and are considered within the scope of the present invention.

Figure 3:
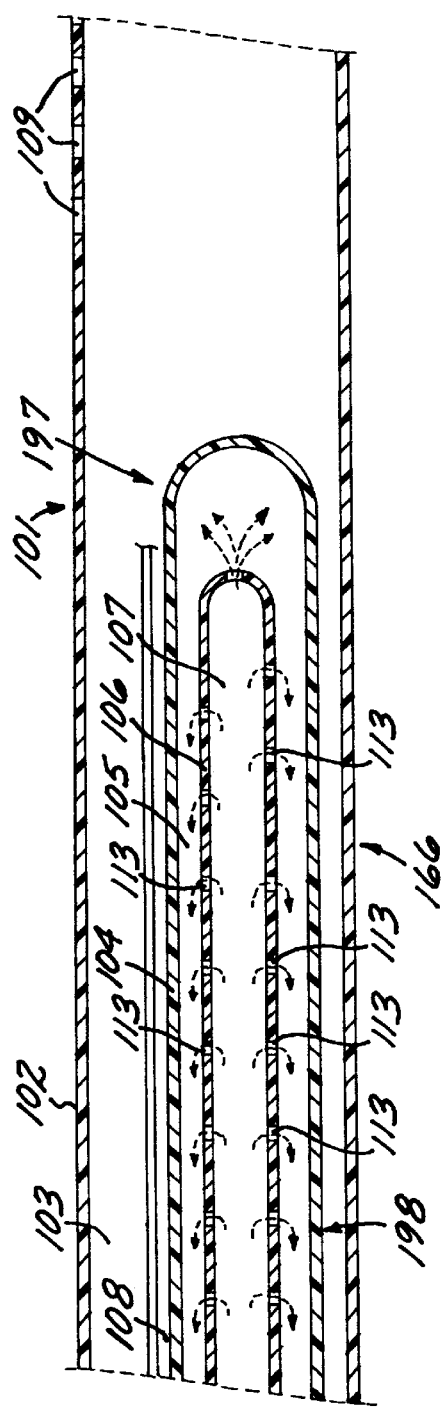
FIG. 3 is a longitudinal cross section of the catheter shaft of FIG. 1 illustrating the catheter shaft assembly.

FIG. 1 illustrates a first embodiment of the present invention which comprises a catheter 100 connected to a fluid transport system 150 and a temperature regulation assembly 160. The catheter 100 is comprised of a catheter body 101 having a multilumen construction that is depicted in FIGS. 2 and 3 and described in detail below.

The catheter shaft 101 is comprised of three tubular members, which extend in a substantially coaxial configuration. The tubular members are collectively referred to as a shaft assembly 166 for ease of illustration and description. The physical relationship of the shaft assembly 166 is for illustrative purposes only and any number of configurations can be used to accomplish desired results, therefore, coaxial, concentric, eccentric, piggyback, parallel and any combination of lumen arrangements should be considered within the scope of the present invention. The shaft assembly 166 and corresponding tubular members may all be made of the same materials or alternatively all different materials or alternatively two of the tubular members may be constructed of the same material and only one tubular body may be manufactured from a different material. Preferably, the shaft assembly 166 is formed from a flexible thermoplastic material, a thermoplastic elastomer or a thermoset elastomer. More specifically, suitable materials for the shaft assembly 166 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the shaft assembly 166 or any one of the tubular members may be made of thin walled metallic tubing or hypotube, such as stainless steel, platinum, titanium, nitinol or Cobalt alloys such as Elgiloy and Carpenter MP 35.

Furthermore, the shaft assembly 166 may be coated with lubricious coatings that aid in the insertion and removal of the catheter as well as aid in hemocompatibility and anticoagulation. The coatings are nonreactive, hydrophilic or hydrophobic. Medicated coatings may also be incorporated which are antithrombogenic, antimicrobial, anticancer, antigrowth factor, growth factor or anti-inflammatory. Examples of such coating are SLIP-COAT and MEDI-COAT made by STS Polymers Henrietta, New York. In addition, the shaft may be coated with echogenic material such as ECHO-COAT also made by STS Polymers Henrietta, New York to aid in tracking and placement of the device with the use of ultrasound.

Referring more specifically to FIG. 2 which is a lateral cross section of the catheter shaft 101 of FIG. 1 taken along line 2—2, what is shown is the multilumen arrangement of the shaft assembly 166. An innermost tubular member 106, has a first lumen 107, that is sized and configured to deliver a heat exchanging medium to the catheter shaft 101. A second tubular member 104 has a second lumen 105 that is sized and configured to serve as a return for the heat exchanging medium. The first tubular member 106 and the second tubular member 104 together serve as a heat exchanging apparatus 198 which circulates the heat exchanging medium within the catheter shaft 101. A third tubular member 102 serves as a housing 197 for the heat exchanging apparatus 198. The internal lumen of the third tubular member is sized and configured for communicating fluid through the catheter shaft 101. The fluid lumen 103, in this illustrative embodiment, is represented by the annular space which is created due to the coaxially extending relationship of the heat exchanging apparatus 198 and the internal lumen 103 of the third tubular member 102. The fluid lumen 103 is isolated from the return lumen 105 by the lumen wall of the second tubular member 104. The lumen wall of the second tubular member 104 represents a heat transfer interface. Fluid travels over the surface of the second tubular member 104 through the fluid lumen 103 where heat transfer occurs. By adjusting the temperature of the heat exchanging apparatus 198, the physician can regulate the temperature of fluid flowing through the catheter shaft 101. Typical fluids that would be used in connection with the present invention include, but are not limited to, blood, water, saline, lysing agents, clot dissolving pharmacological agents, glutamate antagonists, calcium channel blockers, salt based solutions or any other fluid composition or combination as the medical procedure will dictate.

When introduction over a steerable guidewire is preferred, the present invention can be configured to have an internal or external guidewire lumen 108. In alternative embodiments, the guidewire lumen 108 may be incorporated into one of the other lumens to create a more compact design or alternatively a fixed guidewire may be attached to the distal end of the catheter shaft 101, as is well known in the art. Furthermore, the guidewire lumen 108 can also serve as an instrument lumen for the insertion of other medical devices or microcatheters such as peripheral vessel angioplasty catheters, aneurysm clip catheters, dilation catheters, diagnostic catheters, coil delivery catheters or occlusion catheters. The catheters can access the patient's vasculature through perfusion ports 109 or a specific access port sized and configured along the length of the catheter shaft for optimal access. Alternatively, catheters may be advanced out the distal opening 111.

FIG. 3 is a longitudinal cross section of the catheter shaft 101 giving further detail of the physical relationship between the four lumens. The innermost tubular member 106 may be made of any of the materials listed above, and in one preferred embodiment, stainless steel or Nitinol hypotube is used. The hypotube should be sufficiently rigid to sustain the high pressures of compressed gas or liquid, yet flexible enough to enable navigation through a patient's vasculature. With the aforementioned requirements in mind, the hypotube should have a wall thickness of approximately 0.001" to approximately 0.005", a diameter preferably approximately 0.005" to approximately 0.100", more preferably approximately 0.020" to approximately 0.050". The innermost tubular member 106 has at least one output or expansion orifice 113 located along its length which is sized and configured for allowing the expansion or circulation of the heat transfer fluid or medium into the lower pressure region of the second tubular member 104. Preferably, the spacing between the orifices, as well as their size and shape are selected to allow for the appropriate expansion or circulation of the heat exchanging medium so that the appropriate temperature regulation can be obtained under certain pressure conditions. In one preferred embodiment, the spacing between the orifices is selected such that uniform cooling along the length of the shaft is possible. The outputs may be located directly across from one another or alternatively may be staggered along the length of the first tubular member 106. The outputs 113 may be created by mechanically penetrating the exterior surface of the hypotube, or alternatively may be formed by using lasers or by chemical etching.

In one illustrative embodiment, compressed nitrous oxide is delivered through the delivery lumen 107 where expansion occurs upon exiting the outputs 113. The nitrous oxide vaporizes as it expands, cooling the lumen wall of the second tubular member 104. Heat transfer occurs as blood or other fluid flows over the heat transfer interface of the second tubular member 104. Heat transfer can be accomplished through counterflow as illustrated or alternatively by parallel flow.

The distal end of the inner tubular member 106 can also be configured to accommodate a Joule-Thomson valve. Alternatively, only one distal output 113 may be necessary to accomplish the desired results with or without the Joule-Thomson valve. When cold or warm water is used, a closed system can be used by maintaining a higher pressure on the input of the inner tubular member 106 and a lower pressure on the output of the second tubular member 104 to create the desired heat transfer system.

Figure 13:
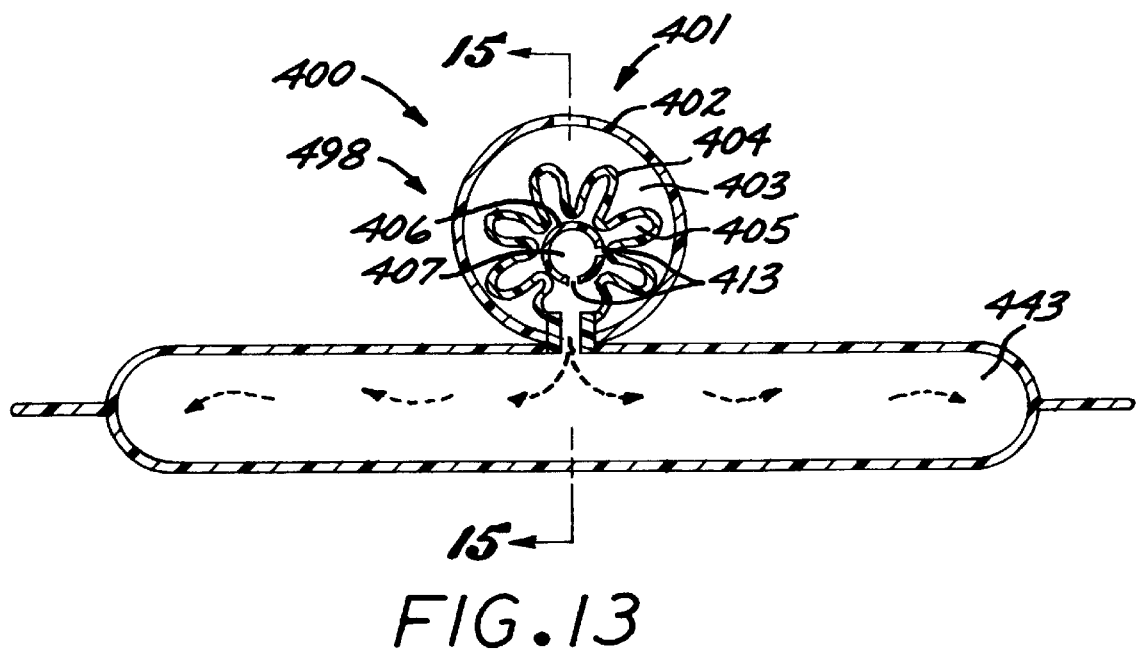
FIG. 13 is a magnified lateral cross section of the catheter of FIG. 12B taken along line 13—13 of FIG. 12B.

The second tubular member 104 can be formed from a variety of materials including the materials discussed above, and in a preferred embodiment, a high thermally conductive material is used. Materials having high thermal conductivity may include, but are not limited to: copper, gold, nitinol, platinum iridium and stainless steel. Furthermore, the second tubular member 104 may be constructed to have fins or other means for enhancing the surface area and corresponding heat transfer ability of the second tubular member 104. For example, in one preferred embodiment the tubular member 104 may be comprised of a substantially cylindrical tube having a plurality of substantially parallel longitudinal corrugations defining a plurality of exterior fluid flow channels and interior return channels for better heat exchange as represented in FIG. 13.

The catheter shaft 101 may be gradually tapering and formed from separate tubing pieces, having the desired lumen configuration or alternatively may be attached end to end and bonded together by methods such as heat welding or adhesive bonding. Alternatively, an end of tubing can be skived away and a TEFLON coated or any other lubricous coated mandrel may be used to promote insertion of one tubing piece into another. The use of TV adhesive bonding and shrink tubing with heat application may be used to ensure that assembled pieces are sealed fluid tight. Alternatively, the catheter shaft 101 may be fabricated by dipping or by composite construction techniques and joined together or the entire catheter shaft 101 may be fabricated integrally by known extrusion techniques. Furthermore, tapered mandrels and a heat source can be used to neck down the outer diameter of the catheter shaft. In alternative embodiments, where it is desirable to have a catheter shaft with one continuous outer diameter, a single piece of tubing can be extruded and necked down to the proper dimensions.

The catheter shaft 101 should be of sufficient length to reach from an external location residing outside the body of a patient to a distant location residing within the internal lumen of the aorta proximate the arch vessels. With the aforementioned length requirements in mind, the overall size of the catheter 100 is preferably approximately 30 to 160 cm, more preferably approximately 50 cm to 120 cm, most preferably approximately 60 to 110 cm in length. The total outside diameter of the catheter shaft 101 should be of minimal size, but of sufficient internal diameter to be able to provide adequate fluid flow as well as adequate heat transfer ability. With the aforementioned diameter requirements in mind, the outside diameter of the catheter shaft 101 is preferably approximately 2 French to 24 French, more preferably approximately 4 French to 18 French, most preferably approximately 6 French to 14 French. In addition, the entire length of the outermost tubular member 102 may be dipped, coated or integrally constructed to have a thermal insulation to decrease thermal conductivity between the catheter 100 and the fluid residing in the vessel of the patient. Alternatively, only part of the catheter shaft 101 may be constructed to have thermal insulation.

Referring back to FIG. 1, the catheter 100 has a series of connectors and fittings attached to the proximal end of the catheter shaft 101 that serve a multitude of functions. A first tube fitting 170 is connected by known means to the output 161 of a temperature regulation assembly 160 for delivering the heat exchange material to the delivery lumen 107 of the catheter 100. The temperature regulation assembly may be comprised of a compressor as is typically associated with a refrigerant type cooling system or an ice bath with computerized temperature regulation assemblies or by thermoelectric cooling with or without an extracorporeal heat sink. A second tube fitting 180 is connected by known means to the input 181 of the temperature regulation assembly 160 to provide a return for the heat exchange material to the temperature regulation assembly 160. In alternative embodiments the return lumen may open to atmosphere or to a separate holding chamber, rather than being recirculated through the temperature regulation assembly 160 as would be typical in a closed cycle.

A fluid transport system 150 has an input 152 and an output 151 in fluid communication with the fluid lumen 103 of the catheter 100. In this illustrative embodiment an external pump 153 is coupled to tube fitting 190 where fluid can be communicated from the patient's artery or vein either peripherally or centrally. For example, in beating heart applications, oxygenated blood can be removed from the artery and circulated through the catheter for cooling of the cerebral circulation. When cannulating the venous system, the deoxygenated blood will need to be oxygenated and cooled before it is returned to the patient.

The term external pump(s) is intended to describe generically all pumps that reside outside of the vasculature of the human body. External pumps may be in the form of centrifugal pumps, peristaltic pumps or roller pumps, which are commonly associated with cardiopulmonary bypass. In addition, mechanical hand pumps, operated through manual pumping mechanisms for emergency resuscitation or trauma can be used, or micropumps located within the catheter body or tube fittings or can be used to reduce priming volume. The fluid transportation system has a luer connector 154 connected to a fluid composition altering source 155 and a second luer connector 156 for sampling fluid within the patient's vasculature or for monitoring pressure, temperature or chemical composition.

Alternatively, in another illustrative embodiment internal pump(s) can be used. The term internal pump is meant to describe generically pumps that reside within a patient's vasculature. Suitable internal pumps adaptable for use in the present invention are described in U.S. Pat. Nos. 4,625,712, 4,944,722, 4,908,012, 4,895,557, 4,846,152, 4,817,586, 5,376,114, 5,695,471, 4,919,647, 5,911,685 and 5,507,629, the complete disclosures of which are hereby incorporated by reference.

A fourth tube connector 140 is in fluid communication with the guidewire lumen 108. The proximal end of tube connector 140 is coupled to a Touhy-Borst fitting 143, hemostasis valve or other suitable fitting capable of facilitating the insertion of guidewire(s) 142 or other medical instruments. A luer connector 144 extends from the Touhy-Borst fitting and is configured for measuring pressure and can also facilitate the insertion of another medical device such as a transducer 141 for measuring flow.

Figure 4:
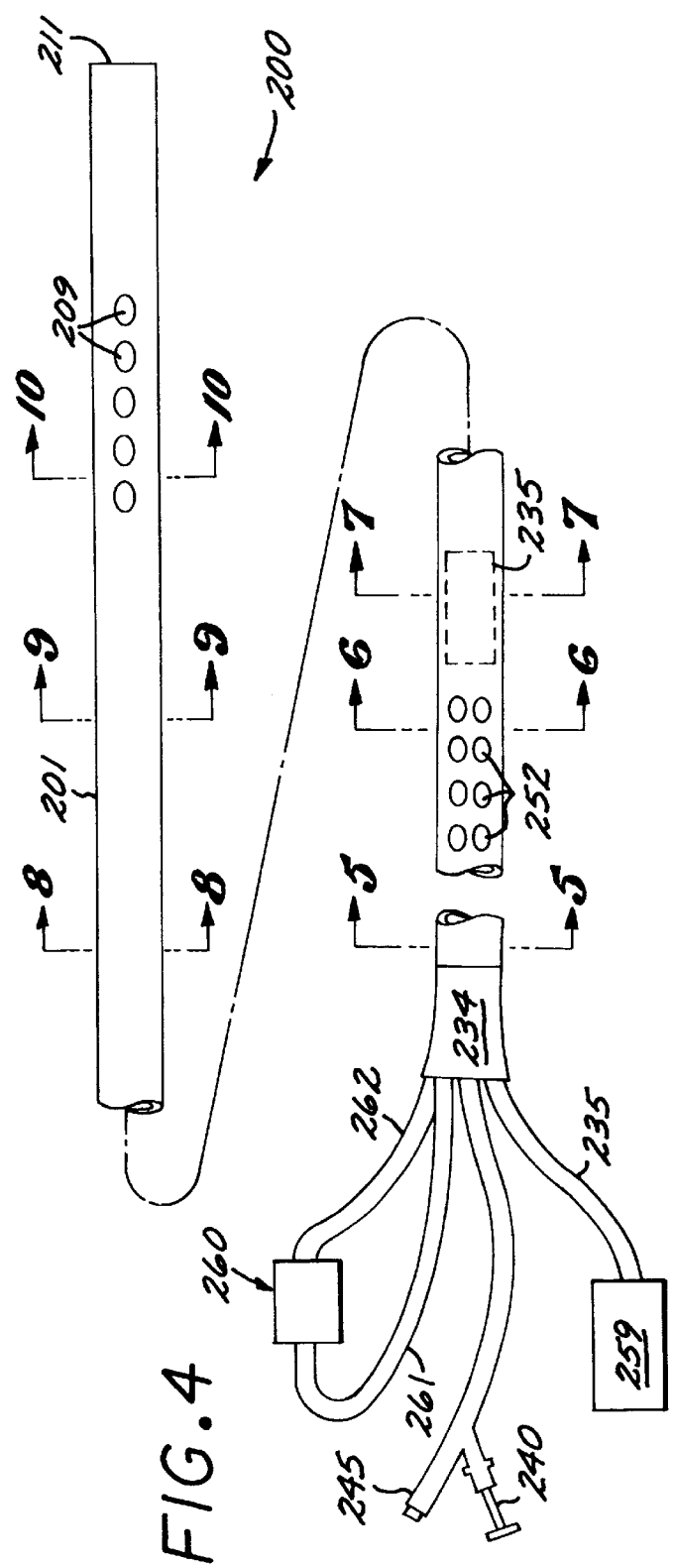
FIG. 4 is a longitudinal cross section of a second embodiment of the present invention illustrating the implementation of an internal impeller pump.

FIG. 4 illustrates a second embodiment of the present invention configured for selectively cooling or warming tissue. What is provided is a selective cooling system comprising a catheter 200 having a fluid transport system 250 and a temperature regulation assembly 260. The catheter 200 is comprised of a catheter shaft/body 201 having multilumen construction. The catheter shaft 201 has a proximal end coupled to a manifold 234 with various working fittings attached to the various lumens of the catheter shaft.

Referring to FIGS. 5 through 10, one illustrative example of the construction of the catheter shaft 201 is shown. The catheter shaft 201 has similar dimensions, and is preferably constructed from the same or similar materials as the shaft assembly 166 described in connection with FIGS. 1–3. The lumen arrangement is for illustrative purposes only and any number of configurations can be used to accomplish desired results, therefore, coaxial, concentric, eccentric, piggyback, parallel or any combination of lumen arrangements should be considered within the scope of the present invention.

Figure 5:
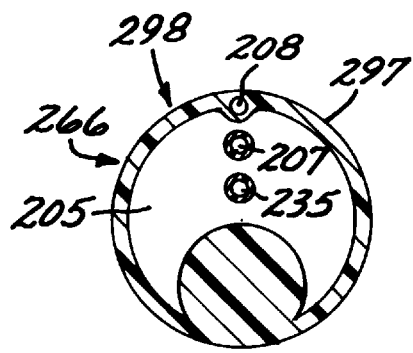
FIG. 5 is a magnified lateral cross section of the catheter of FIG. 4 taken along line 5—5 of FIG. 4.
Figure 6:
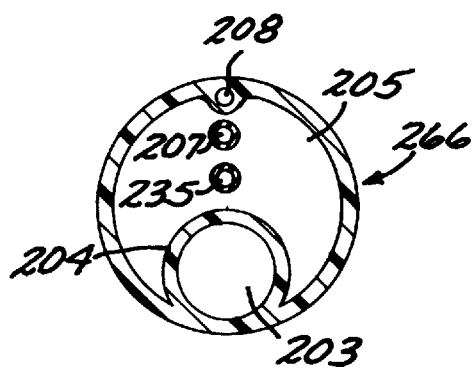
FIG. 6 is a magnified lateral cross section of the catheter of FIG. 4 taken along line 6—6 of FIG. 4.

FIG. 5 is a cross-sectional view of a proximal portion of the catheter shaft 201 taken along line 5—5 of FIG. 4. A delivery lumen 207 is sized and configured to deliver a heat exchanging medium at least in part through the length of the catheter shaft 201. There are a variety of heat exchanging mediums that are well known in the art, including, but not limited to, water, blood, saline and compressed refrigerants, such as freon, liquid nitrogen or nitrous oxide. A return lumen 205 is sized and configured to serve as a return for the heat exchanging medium. The delivery lumen 207 and the return lumen 205 together serve as a heat exchanging apparatus 298 that extends at least in part through the catheter shaft 201 for circulating the heat exchanging medium within the catheter shaft 201. The outermost tubular member 202 serves as a housing 297 for the heat exchanging apparatus 298.

Referring to FIGS. 4 and 5, a power lead 235 extends from a remote power source 259 through the catheter shaft 201 to an internal pump 253. In alternative embodiments, a separate lumen may be provided to house the power lead 235 or, alternatively, the power lead 235 may be integrally formed within the catheter shaft 201. Alternatively, the power source 259 may reside adjacent to the internal pump 253 by using battery power or the like where no power lead 235 would necessary. The placement of the internal pump 253 as it resides within the catheter shaft 201 is more clearly seen by referring to FIG. 7.

Figure 7:
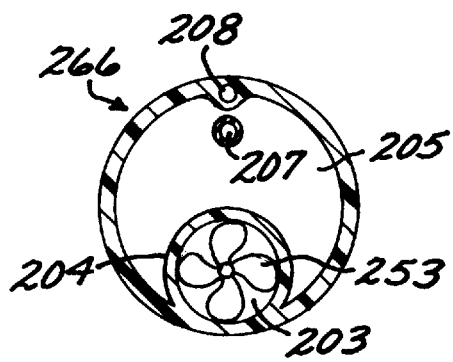
FIG. 7 is a magnified lateral cross section of the catheter of FIG. 4 taken along line 7—7 of FIG. 4.
Figure 8:
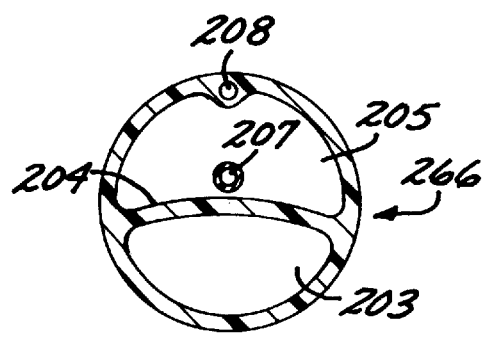
FIG. 8 is a magnified lateral cross section of the catheter of FIG. 4 taken along line 8—8 of FIG. 4.

By referring to FIGS. 4, 7 and 8, the catheter design and component parts are further illustrated. FIGS. 7 and 8 illustrate lateral cross sections of the catheter shaft 201 taken along lines 7—7 and 8—8 of FIG. 4, respectively. An internal pump 253 is in fluid communication with a fluid lumen 203. The internal pump has input 252, in fluid communication with an output for communicating fluid to the fluid lumen 203. The internal pump 253 withdraws blood from a vessel though the input 252 where it is pumped to the fluid lumen 203 and out perfusion ports 209. Fluid such as blood, in addition to other additives, such as lysing agents, clot dissolving pharmacological agents, glutamate antagonists, calcium channel blockers, salt based solutions or any other fluid composition or combination, will travel over the interface 204 where temperature can be controlled and heat transfer occurs.

A guidewire lumen 208 is also provided to facilitate the insertion of a steerable guidewire. In alternative embodiments, the guidewire lumen 208 may be incorporated into one of the other lumens to create a more compact design or a fixed guidewire may be attached to the distal end of the catheter shaft 201, as is well known in the art. Furthermore, the guidewire lumen can serve to facilitate the insertion of other medical devices or microcatheters such as carotid stent catheters, aneurysm clip catheters, dilation catheters, diagnostic catheters, coil delivery catheters or occlusion catheters that access the patient's vasculature through perfusion ports 209 or a specific access port designated along the length of the catheter shaft or out the distal opening 211.

Figure 9:
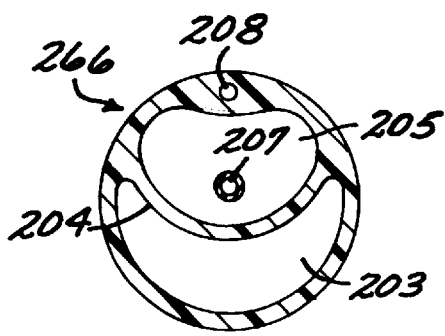
FIG. 9 is a magnified lateral cross section of the catheter of FIG. 4 taken along line 9—9 of FIG. 4.
Figure 10:
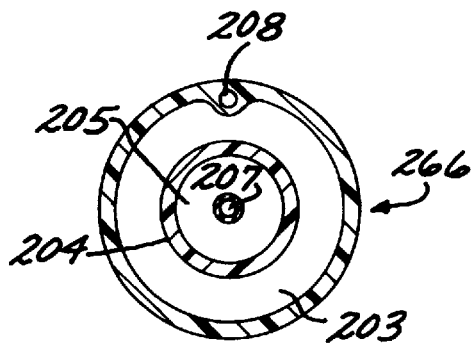
FIG. 10 is a magnified lateral cross section of the catheter of FIG. 4 taken along line 10—10 of FIG. 4.

FIGS. 9 and 10 illustrate the catheter's lumen configuration as it transitions in a distal direction to maximize heat transfer surface area. The location of the cross sections is for illustrative purposes only and in a preferred embodiment the transitional cross sections are positioned closer to the proximal end of the catheter shaft 201 so that the surface area of the fluid lumen 203 is in greatest contact with the heat exchange interface which is defined by the lumen wall of the second tubular member 204.

The catheter shaft 201 may be gradually tapering and formed from separate tubing pieces having the desired lumen configuration or, alternatively, may be attached end to end and bonded together by methods such as heat welding or adhesive bonding. Alternatively, an end of tubing can be skived away and a TEFLON coated or other lubricous coated mandrel may be used to promote insertion of one tubing piece into another. UV adhesive bonding and shrink tubing with heat application may be used to ensure that assembled pieces are sealed fluid tight. Alternatively, the catheter shaft 201 may be fabricated by dipping or by composite construction techniques and joined together or the entire catheter shaft 201 may be fabricated integrally by known extrusion techniques. Furthermore, the use of tapered mandrels and a heat source can be used to neck down the outer diameter of the catheter shaft. In alternative embodiments, where it is desirable to have a catheter shaft with one continuous outer diameter, a single piece of tubing can be extruded and necked down to the proper dimensions.

The catheter shaft 201 should be of sufficient length to reach from an external location residing outside the body of a patient to a distant location residing within the internal lumen of the aorta proximate the arch vessels. With the aforementioned length requirements in mind, the overall size of the catheter 200 is preferably approximately 30 to 160 cm, more preferably approximately 50 cm to 120 cm, most preferably approximately 60 to 110 cm in length. The total outside diameter of the catheter shaft 101 should be of minimal size, but of sufficient internal diameter to be able to provide adequate fluid flow as well as adequate heat transfer ability. With the aforementioned diameter requirements in mind, the outside diameter of the catheter shaft 201 is preferably approximately 2 French to 24 French, more preferably approximately 4 French to 18 French, most preferably approximately 6 French to 14 French. In addition, the catheter shaft 201 may be dipped, coated or integrally constructed to have a thermal insulation to decrease thermal conductivity between the catheter 201 and the fluid residing in the vessel of the patient. Alternatively, only part of the catheter shaft 201 may be constructed to have thermal insulation.

Referring back to FIG. 4 the catheter 200 has a manifold 234 with various working fittings attached to the various lumens of the catheter shaft 201. A tube fitting 261 is connected by known means to the output of a temperature regulation assembly 260 for delivering the heat exchange material to the delivery lumen 207. In one illustrative embodiment, a compressed refrigerant such as freon, liquid nitrogen or nitrous oxide is used to deliver the heat exchange material to the delivery lumen 207. In another illustrative embodiment cold water is used. A second tube fitting 262 is connected by known means to the input of the temperature regulation assembly 260 as a return for the heat exchange material to the temperature regulation assembly 260. In alternative embodiments, the return lumen may open to atmosphere or to a separate holding chamber rather than being recirculated through the temperature regulation assembly 260.

A Touhy-Borst fitting 240, hemostasis valve or other suitable fitting capable of facilitating insertion of other medical devices or instruments is in fluid communication with the guidewire lumen 208. Furthermore, a luer connector 245 extends from the Touhy-Borst fitting and is configured for measuring pressure, temperature and chemical composition by way of ports 209 or the end opening 211.

Figure 11:
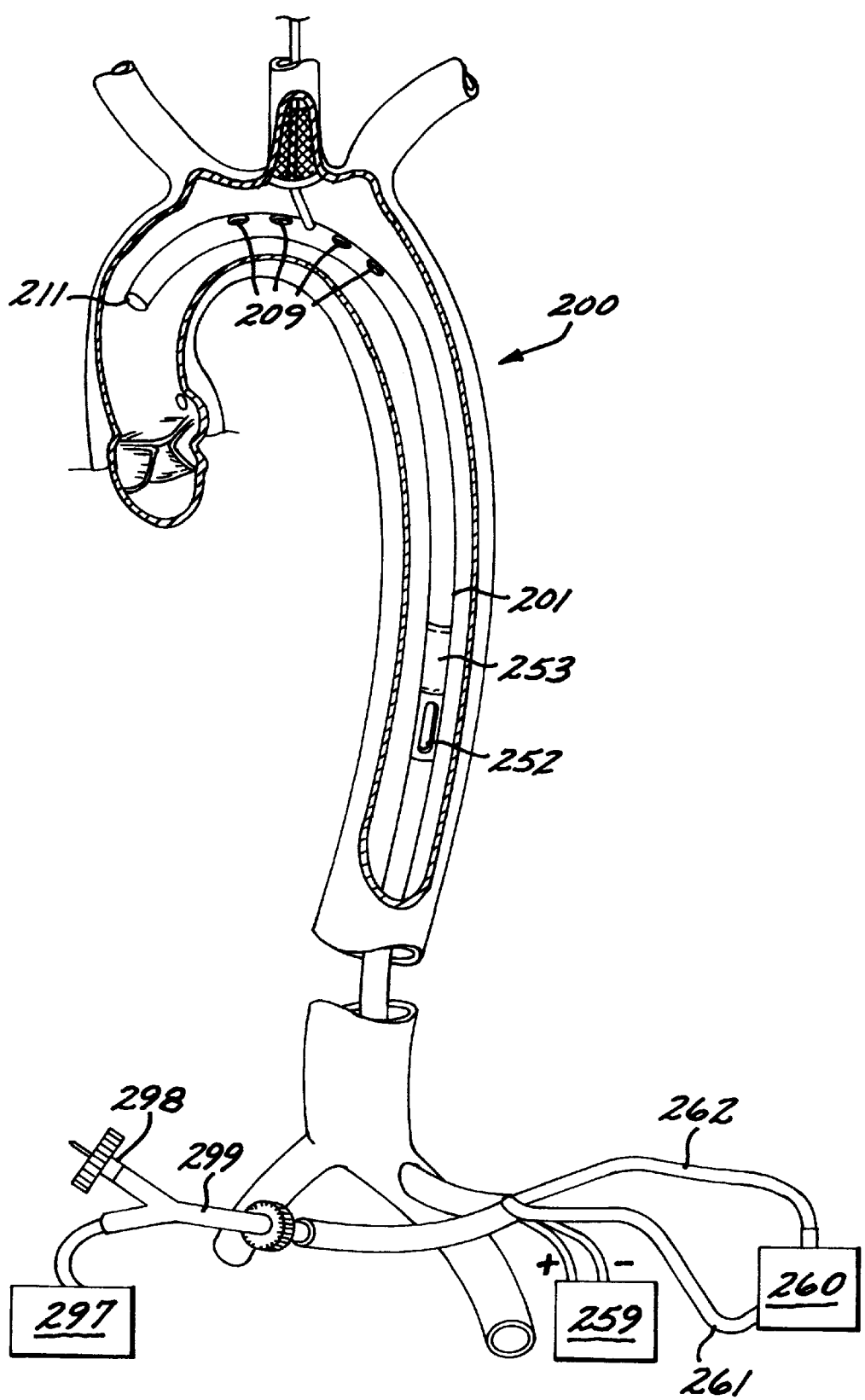
FIG. 11 is a third embodiment of the present invention deployed within a patient's aorta and configured for receiving a second medical instrument for accessing the cerebral circulation.

FIG. 11 illustrates a third embodiment of the present invention where the catheter of FIG. 4 is in an operative position in a patient's aorta. The catheter 200 is multifunctional and is adapted to perform effectively in a variety of medical situations. For example, in an emergency situation, such as stroke, trauma, resuscitation or closed head injury the catheter is designed for ease of insertion into a peripheral vessel for rapid cooling of the brain. Alternatively, during an elective cardiac surgery including traditional stopped heart, beating heart or minimally invasive stopped heart surgery, or for neurosurgery the catheter is effective for rapid cooling of the brain to create a cerebral protective environment. Methods for introducing the catheter 200 include percutaneous insertion, arterial cutdown, Seldinger technique over a guidewire, as well as an aortotomy with a purse string suture. The catheter can be introduced through any peripheral access vessel including the subdlavian, radial, iliac, femoral or brachial artery or alternatively through an intercostal space, median sternotomy, minithoracotomy or left thoracotomy. Once inserted, the catheter is navigated into an operative position until blood perfusion ports 209 are proximate or adjacent to the arch vessels. In order to selectively cool the brain separately from the rest of the body rapidly and efficiently, the internal pump 253 withdraws blood into the input 252 and directs it into the fluid lumen 203 where it is cooled along the length of the catheter shaft 201. The blood is cooled to the optimal temperature and exits out ports 209 where cooled fluid is delivered to the cerebral circulation in an efficient manner. Optionally, the temperature can be measured by incorporating temperature transducers or thermocouples into the catheter. The catheter stays in the correct position due to the sufficient rigidity and pre-set curvature of the catheter shaft 201, which is especially beneficial in beating heart applications. Additional reinforcement can be used in the area of the curvature to help support the shaft.

The aortic catheter 200 of FIG. 11 is also configured for supporting the use of other medical devices. Once the aortic catheter 200 is navigated into the operative position over a guidewire, the guidewire is removed through the Touhy-Borst fitting and another medical instrument 299 is inserted therethrough, also over a guidewire. The present invention is intended to be compatible with rapid exchange and over the wire catheters. In this current illustrative embodiment, a carotid stent catheter is employed having an additional guidewire fitting and inflation fitting. The medical device 299 may access any number of organs or vessels and therefore any number of ports may be implemented to facilitate the desired procedure. For example, if the heart is the target organ, port 211 may be the optimal port to reach the heart. Alternatively, if the cerebral vasculature or carotid arteries are the target area(s), then ports 209, which also serve as perfusion ports, might be the most desirable port(s) to use. In addition, in other alternative embodiments another port designed especially for other medical instruments can be implemented. Other medical devices suitable for insertion through catheter 200 include, angioplasty balloon catheters, stent catheters, atherectomy catheters, transmyocardial revascularization catheters, pigtail catheters, in stent restenosis removal catheters, stent removal catheters, diagnostic catheters, angiogram catheters, carotid stent catheters, coil delivery catheters, embolization therapy catheters, drug delivery catheters or secondary temperature regulation or measuring catheters or any other medical device. The catheter 200 enables the creation of a neuroprotective environment by implementing the use of hypothermia as a co-therapy or as an adjunct to elective neurosurgery or cardiac surgery.

Figure 12A:
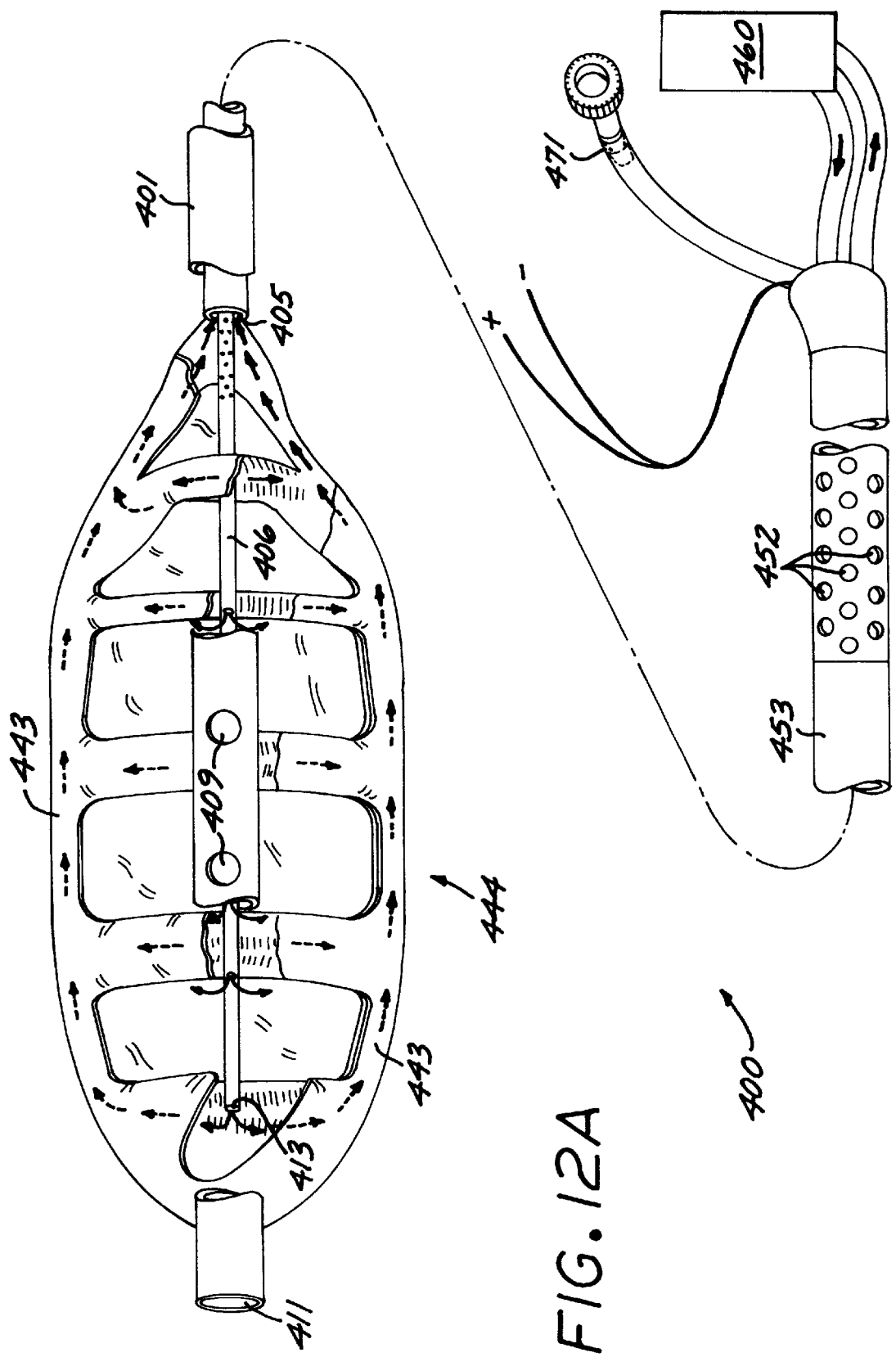
FIG. 12A is a fourth embodiment of the present invention having an expandable membrane configured for isolating flow to the cerebral circulation.
Figure 12B:
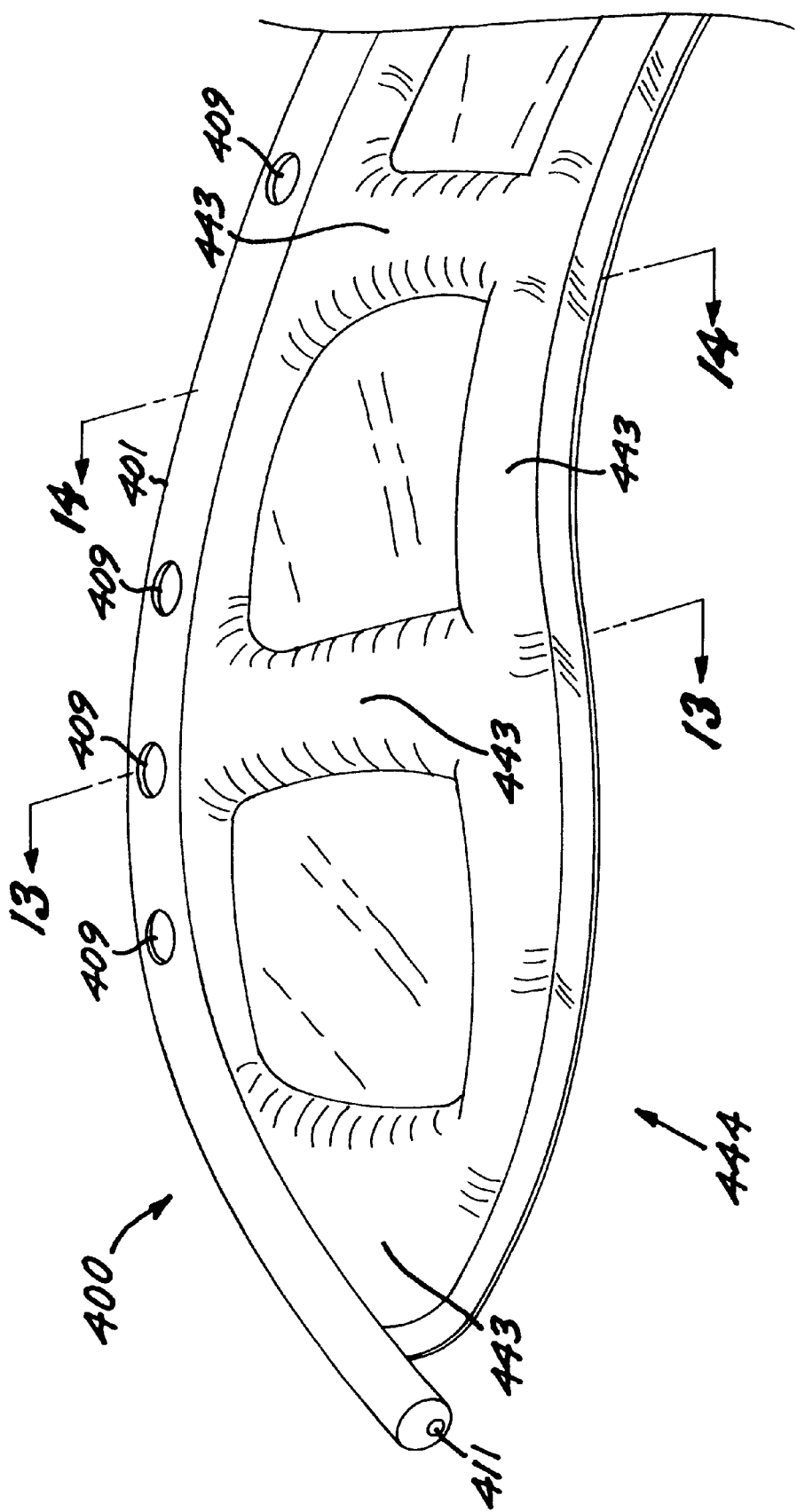
FIG. 12B is a magnified perspective view of the expandable membrane of FIG. 12A.

FIGS. 12A and 12B illustrate a fourth embodiment of the present invention having an aortic isolator 444 in the form of an expandable membrane or mesh. Other forms of aortic isolators, which are in the form of shunt isolators, can be found in commonly owned, copending U.S. patent application No. 09/212,580 filed Dec. 14, 1998, claiming the benefit of U.S. provisional application No. 60/069,470 filed, Dec. 15, 1997.

In general, the expandable membrane 444 will have an undeployed or collapsed state which is not substantially larger than the external diameter of the catheter shaft and an expanded or deployed state configured for optimal cooling or warming in the aortic arch by creating isolated flow segmentation. The expandable membrane 444 may be deployed from an exterior surface of the catheter shaft 401 or from within a lumen of the catheter shaft.

The expandable membrane 444 is coupled to an exterior surface of the catheter shaft 401. Any number of mechanisms and techniques may be used to attach the expandable membrane to the catheter shaft 401 including, but not limited to, heat bonding, molding, extruding and/or adhesives. In alternative embodiments, the expandable membrane may be integrally built into the catheter shaft 401. The expandable membrane 444 may be mounted on the catheter shaft 401 such that the expandable membrane 444 is centered relative to the catheter shaft or alternatively may be offset. In addition, the membrane 444 may be mounted on the surface of the catheter shaft 401 or may expand from a middle portion of the catheter shaft 401 where two separate membranes are used. The expandable membrane 444 comprises one or more biasing rib(s) 801 inflatable chambers or selectively deployable shroud(s). The inflatable chambers 443 may be relatively non-compliant, or compliant, exhibiting elastic behavior after initial inflation to closely fit the aortic lumen size and curvature. For a complete description of expandable membranes and the structural features thereof reference is made to commonly owned, U.S. Pat. No. 6,371,935 filed Aug. 20, 1999, claiming the benefit of the U.S. provisional patent application No. 60/116,836 filed Jan. 22, 1999, and commonly owned, co-pending patent application filed Jan. 22, 2000, entitled Aortic Catheter with Flow Divider and Methods of Preventing Cerebral Embolization, by Macoviak et al., the complete disclosures of which are hereby incorporated by reference herein their entirety.

The catheter shaft has at least one perfusion pdt(s) 409 located along the surface of the catheter shaft 401 for directing fluid to the vessels of a patient. The ports 409 may be sized and configured to direct fluid at a specific angle or direction. For example, the ports may direct flow upstream, downstream, toward the arch vessels, away from the arch vessels or any combination thereof. The materials suitable for the catheter shaft, as well as the method of assembly, are substantially similar to the materials and construction as discussed in connection with the catheter assembly 166 of FIGS. 1–3, the complete description of which is incorporated into this illustrative embodiment.

Figure 14:
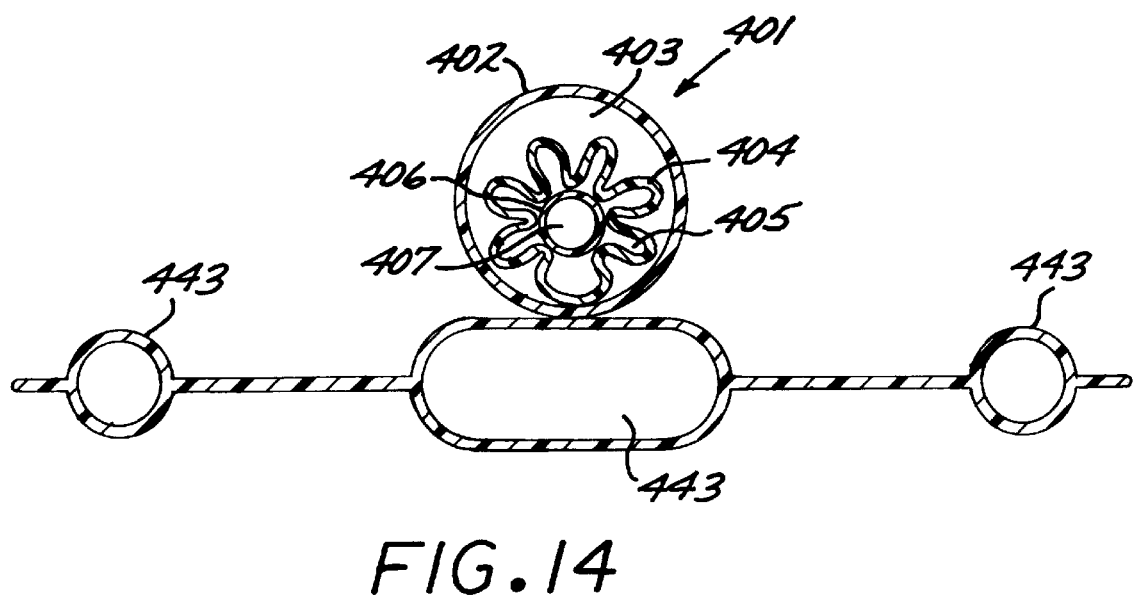
FIG. 14 is a magnified lateral cross section of the catheter of FIG. 12B taken along line 14—14 of FIG. 12B.
Figure 15:
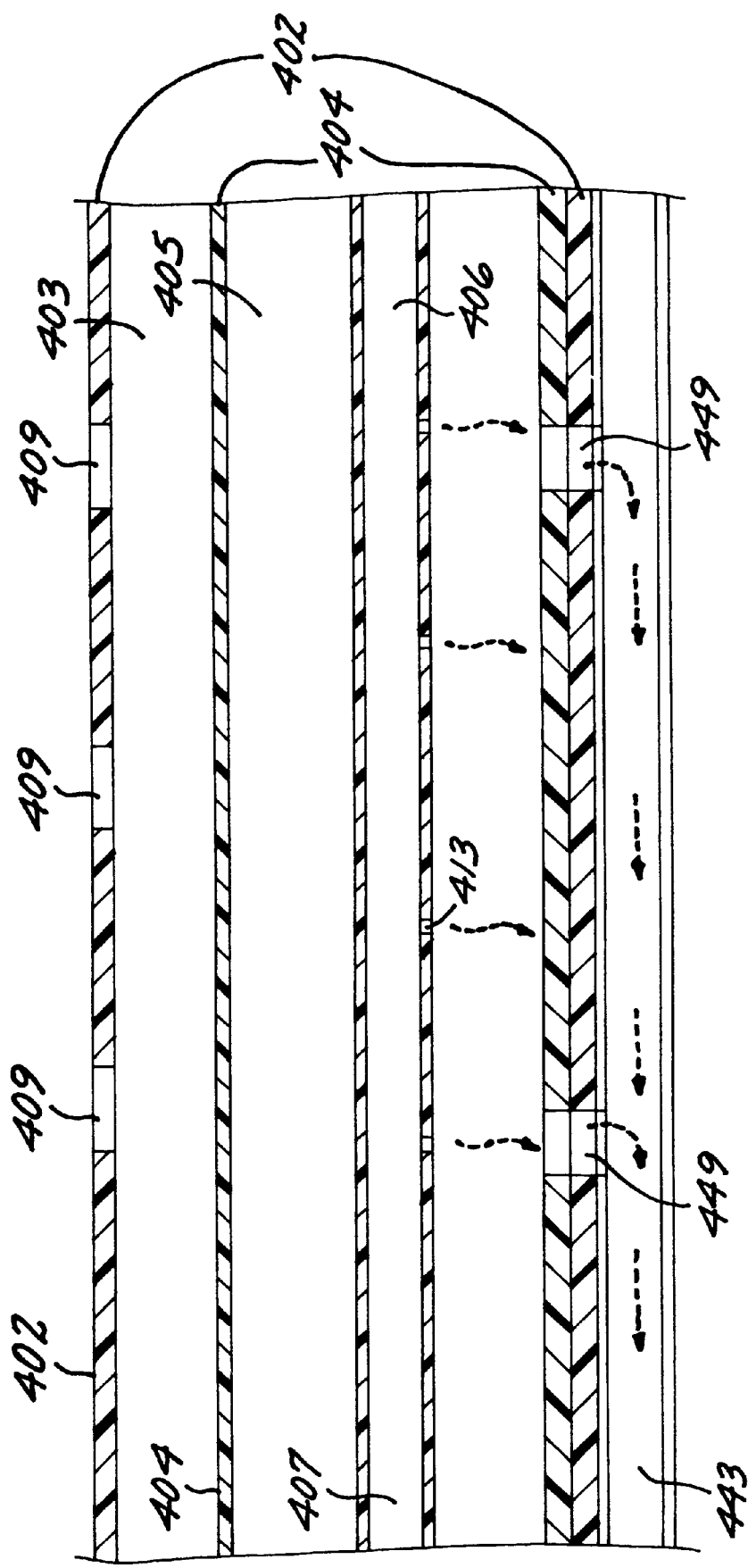
FIG. 15 is a magnified cross section of the catheter of FIG. 13 taken along line 15—15.

FIGS. 13 through 15 are various cross sections of the catheter 400 illustrating the relationship of the various catheter lumens. A first tubular member 406, preferably constructed from stainless steel hypotube, extends at least in part through the catheter shaft 401 and has an internal lumen 407 configured for communicating a heat exchanging medium to the catheter shaft. The hypotube may have a series of ports 413. A second tubular member 404, also extends at least in part through the catheter shaft 401 and has an internal lumen 405 which serves as a return lumen for the heat exchanging medium as it is released from the internal lumen 407 of the first tubular member 406. Together, the first tubular member and the second tubular member comprise an internal heat exchanging apparatus 498 that resides within the fluid lumen 403 of a third tubular member 402. The heat exchanging apparatus extends through the drive shaft of the internal pump or impeller pump 453. Blood is pumped through the fluid lumen 403 where it is cooled or warmed as it travels over the surface of the longitudinally extending convoluted heat exchange interface, which is defined by the surface of the second tubular member 404.

The expandable membrane 444 has one or more inflatable chambers 443 that are in fluid communication with the return lumen 405. The heat exchanging medium is released from ports 413, where it is allowed to expand into channel(s) 449 which are in fluid communication with the interior of the expandable member 444. As the heat exchanging medium is released into the inflatable channels 443, the expandable member 444 becomes inflated and cold, and is adapted to serve as a heat exchanging apparatus as well as a fluid flow divider. The fluid flow divider 444 may be constructed to be thermally insulated on at least one surface so that only the fluid flowing over the top surface of the expandable membrane is cooled while fluid from the beating heart that passes on the underside of the expandable membrane 444 is not altered in temperature. For example, incorporation of an insulation barrier such as an air pocket(s), or incorporation of a material with low thermal conductivity including elastomers, polymer foams or cork can be used. Alternatively, a thermally reflective material can be used, or any combination of the foregoing can be implemented.

Figure 16:
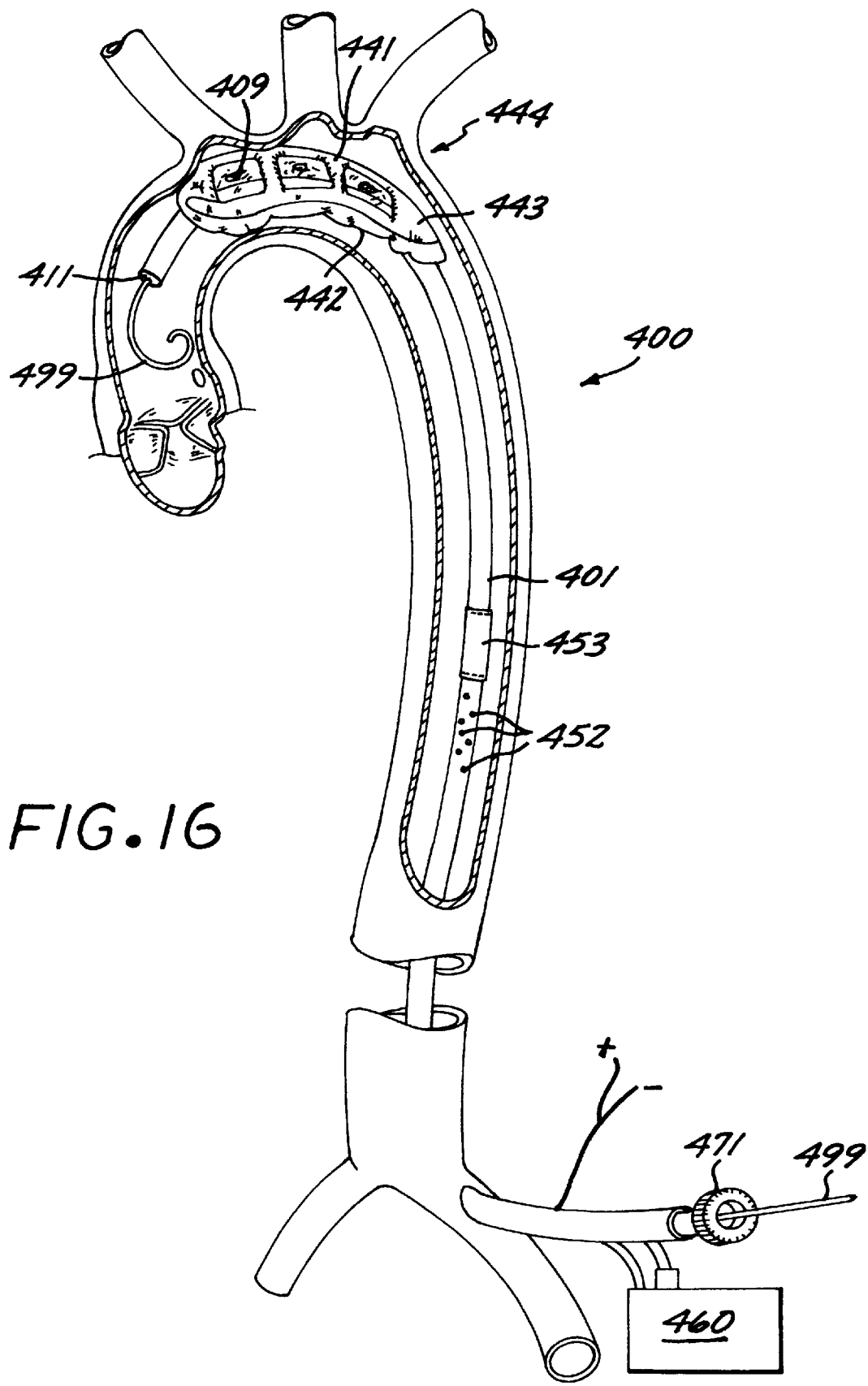
FIG. 16 is an illustration of the catheter of FIG. 12A deployed within a patient's aorta.

FIG. 16 illustrates the catheter of FIGS. 12A and 12B deployed within a patient's aorta. The catheter 400 can be introduced through any peripheral access vessel including the subclavian, radial, iliac, femoral or brachial artery or alternatively through an intercostal space, median sternotomy, minithoracotomy or left thoracotomy. Methods for introducing the catheter include arterial cutdown, Seldinger technique over a guidewire 499 or percutaneously. The catheter 400 is navigated through the aorta until ports 409 are proximate or adjacent to the arch vessels. To selectively cool the brain rapidly and efficiently separately from the rest of the body, an internal pump 453, with internal power means located adjacent thereto, withdraws oxygenated blood from the patient's vessel to a fluid lumen 403. The blood is cooled to the optimal temperature as it travels over the surface of a second tubular member 404, which defines a heat exchanging interface. The blood is then directed out perfusion ports 409 to selectively cool the cerebral circulation.

The wall of the second tubular member 404 is cooled as the heat transfer medium is released from the delivery lumen 407 into the return lumen 405 of the second tubular member 406. The source of the heat exchanging medium is from a temperature regulation assembly 460. A temperature monitor such as a themocouple can be built into the assembly or a separate lumen can be provided to measure temperature within the catheter lumen or proximate the arch vessels.

As was described above, the expandable membrane 444 can also serve as a heat exchanging element. The delivery lumen 407 has multiple outputs 413 located near the distal end of the catheter 400, which are positioned to allow the expansion of the heat exchanging medium directly into the expandable membrane 444 with or without a Joule-Thomson valve. In this manner, the expandable membrane 444 becomes an expansion area for the heat exchanging medium. The superior surface 441, of the expandable membrane 444, faces the arch vessels when it is in the proper position and can be used to selectively cool or warm fluid as it passes over the surface and is directed to the arch vessels. The inferior surface 442 of the expandable membrane 444 can be thermally treated so that heat transfer does not occur across the inferior surface to prevent whole body hypothermia. Alternatively, no fluid lumen may be incorporated into the catheter 400 providing for a more compact design wherein the expandable membrane alone may serve as the heat exchanging interface such that blood cools as it travels over the surface of the expandable membrane 444.

The aortic catheter 400 of FIG. 16 is also configured for supporting the use of other medical devices. The aortic catheter 400 is navigated into the operative position over a guidewire. The guidewire is removed and another medical instrument 499 can be inserted through Touhy-Borst fitting 471. In alternative embodiments, an additional lumen can be provided for the insertion of other medical devices. The guidewire 499 may stay in place serving to support the catheter 400 when in the operative position as illustrated in FIG. 16 so that the expandable membrane stays in the proper position. The medical device may access any number of organs or vessels and therefore any number of ports may be implemented to facilitate the desired procedure. For example, if the heart is the target organ, port 411 may be the optimal port to reach the heart. Alternatively, if the cerebral vasculature or carotid arteries are the target area, then ports 409, which also serve as perfusion ports, might be the most desirable port(s) to use. In addition, when an additional medical device lumen is provided, another port designed especially for other medical instruments can be implemented. Other medical devices which may be inserted through catheter the 400 include, angioplasty balloon catheters, stent catheters, atherectomy catheters, transmyocardial revascularization catheters, pigtail catheters, in-stent restenosis removal catheters, stent removal catheters, diagnostic catheters, angiogram catheters, carotid stent catheters, aneurysm clip catheters, coil delivery catheters, drug delivery catheters or secondary temperature regulation or measuring catheters or any other medical device.

Figure 17:
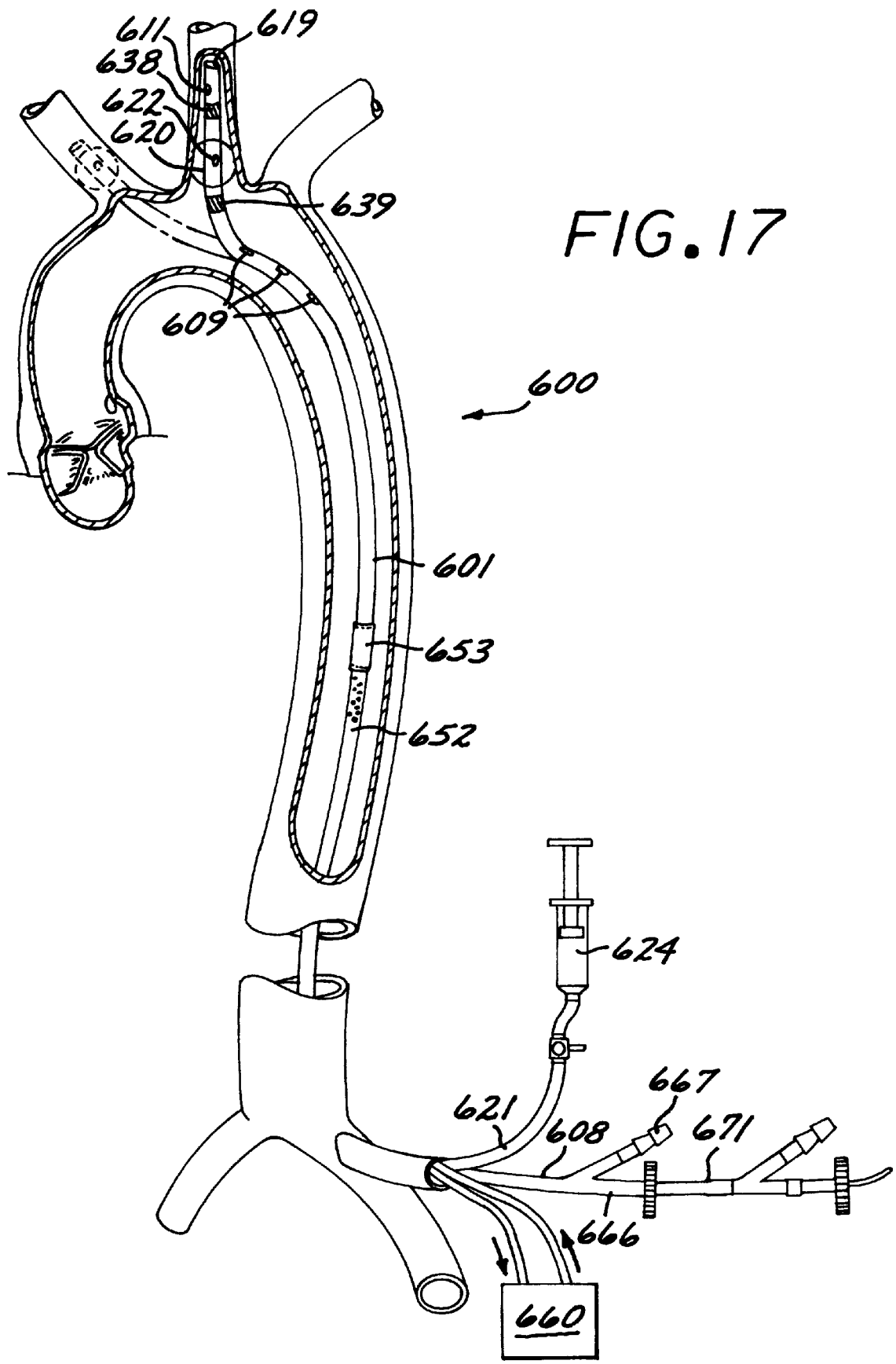
FIG. 17 is a sixth embodiment of the present invention deployed within a patient's aorta having an occluding member located near the distal end of the catheter shaft for stabilizing the catheter shaft in an operative position and configured for delivering a treated fluid to the cerebral circulation to selectively cool cerebral tissue through an internal or extracorporeal heat exchanger.

FIG. 17 is a sixth embodiment of the present invention having a catheter shaft deployed within a patient's aorta having an expandable membrane in the form of an occluding member located near the distal end of the catheter shaft for stabilizing the catheter in an operative position and configured for delivering a treated fluid to the cerebral circulation to selectively cool cerebral tissue through an internal heat exchanger and an internal impeller pump.

The catheter 600 has a catheter shaft 601 that can be constructed from the same materials and same component parts as described in connection with any of the above described embodiments. Without limiting the foregoing, the catheter shaft 601 is preferably formed of a flexible thermoplastic material, a thermoplastic elastomer or a thermoset elastomer. The catheter shaft 601 may be fabricated separately by known extrusion methods and joined together end to end, for example by heat welding or by adhesive bonding. Alternatively, the catheter shaft 601 may be fabricated by dipping or by composite construction techniques and joined together or the entire catheter shaft 601 may be fabricated integrally. Suitable materials for the elongated catheter shaft 602 include, but are not limited to, polyvinylchloride, polyurethane, polyethylene, polypropylene, polyamides (nylons), polyesters, silicone, latex, and alloys or copolymers thereof, as well as braided, coiled or counterwound wire or filament reinforced composites.

An occlusion member 620 is mounted on the distal portion of the catheter shaft 601. The occlusion member 620, in this embodiment, is in the form of an expandable membrane or inflatable balloon. The inflatable balloon is bonded to the catheter shaft 601 by heat welding or by using an adhesive or a combination of both. Suitable materials for manufacturing the inflatable balloon 620 include flexible polymers and elastomers, which include, but are not limited to, polyvinylchloride, polyurethane, polyethylene, polypropylene, polyamides (nylons), polyesters, latex, silicone, and alloys, copolymers and reinforced composites thereof. In addition, the outer surface of the occlusion balloon 620 may include a friction increasing coating or texture to increase friction when deployed in the patient's vasculature. The occlusion member 620 has a deflated state, in which the diameter of the occlusion member 620 is preferably not much larger than the diameter of the catheter shaft 601, and an inflated state, in which the occlusion member 620 expands to a diameter sufficient to stabilize the catheter shaft 601 within the patient's vasculature. FIG. 17 illustrates the occlusion member 620 deployed in a proximal portion of the left common carotid artery. In alternative embodiments, the brachiocephalic artery may be occluded or the left subclavian artery can be occluded as well as any combination thereof through the implementation of one or more occluding members. For use in adult human patients, the occlusion member 620 preferably has an inflated outer diameter of approximately 0.2 cm to 3.0 cm. In alternative embodiments, external or internal valves can be used or an expandable distal end of the catheter can be deployed through an actuation member or self-expanding nitinol.

Preferably, the aortic catheter 600 includes one or more markers, which may include radiopaque markers and/or sonoreflective markers, to enhance imaging of the aortic catheter 600 using fluoroscopy or ultrasound, such as transesophageal echocardiography (TEE). In this illustrative embodiment, the aortic catheter 600 includes a distal radiopaque marker 638 positioned near the distal end of the catheter shaft 601, and a proximal radiopaque marker 639 positioned near the proximal edge of the occlusion member 620. Each of the radiopaque markers may be made of a ring of dense radiopaque metal, such as gold, platinum, tantalum, tungsten or alloys thereof, or a ring of a polymer or adhesive material heavily loaded with a radiopaque filler material.

One method of using the catheter 600 of the present invention is to insert the catheter into a peripheral artery such as the femoral, iliac, brachial or radial artery through known techniques including over a guidewire and introducer or alternatively by the Seldinger technique. When applicable, the present invention can also be implemented in conjunction with a median sternotomy or thoracotomy. The catheter is navigated into an operative position within the patient's vasculature until the occlusion member 620 is positioned in one of the aortic arch vessels. Proper confirmation can be established through known positioning techniques common to one of ordinary skill in the art including TEE, fluoroscopy or ultrasound. The occlusion member 620 is actuated through an inflation lumen 621, in fluid communication with an inflation port 622, which resides in the interior of the occlusion member 620. An inflation medium 624, such as saline mixed with a radiopaque contrast medium may be used to inflate the occlusion member 620.

Blood is directed into the inlet 652 and communicated through the catheter shaft by an internal pump 653 through a fluid lumen where heat exchange occurs along a heat transfer interface as was described in detail in connection with any of the previously described embodiments. The heat exchanging medium is kept at the desired temperature by appropriately adjusting the temperature regulation assembly 660. The catheter shaft 601 remains stabilized even during pressure variations within the aorta that occur during the cardiac cycle due to the stabilizing properties of the occlusion member 620. In alternative embodiments, perfusion ports 619 can also be implemented to augment fluid perfusion distal to the occlusion member 620 through additional ports 619 and 611.

Distal port(s) 619 are in fluid communication with a guidewire lumen 608 having a proximal Y-fitting comprising a Touhy-Borst fitting 666 and luer fitting or barb connector 667. In addition to serving as a guidewire lumen, the lumen is also configured for facilitating the insertion of other medical devices 671 including, coil delivery catheters, drug delivery catheters, suction catheters or any other catheter or medical instrument to be used in the treatment of stroke, closed head trauma or neurosurgery. The luer connector 667 can be used to deliver neuropreservative agents to an area distal to the occlusion member 620 or to withdraw fluid from an area distal to the occlusion member 620.

FIGS 18–20 illustrate a seventh embodiment of the present invention configured for cooling or warming a fluid within a catheter body. In this illustrative embodiment, the heat exchanging apparatus is capable of cooling fluid on the inner surface and outer surface of the heat exchange interface. The catheter 700 has an internal fluid transport system 750 and a temperature regulation assembly 760. The catheter 700 is comprised of a catheter shaft/body 701 having a multilumen construction that is shown in more detail in FIG. 19.

The catheter shaft 701 is comprised of three tubular members, which extend in a substantially coaxial configuration. The tubular members are collectively referred to as a shaft assembly 766 for ease of illustration and description. The physical relationship of the shaft assembly 766 is for illustrative purposes only and any number of configurations can be used to accomplish desired results, therefore, coaxial, concentric, eccentric, piggyback, parallel and any combination of lumen arrangements should be considered within the scope of the present invention. The shaft assembly 766 and corresponding tubular members may all be made of the same materials or alternatively all different materials or alternatively two of the tubular members may be constructed of the same material and only one tubular body is manufactured from a different material. Preferably, the shaft assembly 766 is formed from a flexible thermoplastic material, a thermoplastic elastomer or a thermoset elastomer. More specifically, suitable materials for the shaft assembly 766 include, but are not limited to, PEBAX, PVC, PET, polystyrene, polyvinylchloride, polyurethane, polyethylene, polypropylene, polyamides (nylons), copolymers, polyesters, silicone, latex, and combinations thereof, as well as braided, coiled or counterwound wire reinforcement or filament reinforced composites. Alternatively, or in combination therewith, the shaft assembly 766 or any one of the tubular members may be made of thin walled metallic tubing or hypotube, such as stainless steel, platinum, titanium, Nitinol alloys or Cobalt alloys such as Elgiloy and Carpenter MP 35.

Furthermore, the shaft assembly 766 may be coated with lubricious coatings that aid in the insertion and removal of the catheter as well as aid in hemocompatibility and anticoagulation. The coatings may be nonreactive and hydrophilic or hydrophobic. Medicated coatings may also be incorporated which are antithrombogenic, antimicrobial, anticancer, antigrowth factor, growth factor or anti-inflammatory. Examples of such coating are SLIP-COAT and MEDI-COAT made by STS Polymers Henrietta, New York. In addition, the shaft may be coated with echogenic material such as ECHO-COAT also made by STS Polymers Henrietta, N.Y. to aid in tracking and placement of the device with the use of ultrasound.

The first tubular member 706, represented by the innermost tubular member, has a first lumen 707 that is sized and configured to deliver a heat exchanging medium to the interior of the catheter shaft 701. There are a variety of heat exchanging mediums that are well known in the art, including, but not limited to, water, blood, saline and compressed refrigerants, such as freon, liquid nitrogen or nitrous oxide. A second tubular member 704 has a second lumen(s) 705 that is sized and configured to serve as a return for the heat exchanging medium. The first tubular member 706 and the second tubular member 707 together serve as a heat exchanging apparatus 798 that extends at least in part through the third tubular member 702. The third tubular member 702 is represented by the outermost tubular member and serves as a housing 797 for the heat exchanging apparatus 798. The third tubular member has an internal lumen 703, which is sized and configured to communicate a fluid through the catheter shaft to an area internal to the patient. The fluid lumen 703, is defined by the annular space created between the heat exchanging apparatus 798 and the internal surface of the third tubular member wall. Fluid such as blood, tPA, lysing agents, clot dissolving pharmacological agents, glutamate antagonists, calcium channel blockers, salt based solutions or any other fluid composition or combination may travel over and within the surface of the second tubular member 704 through the fluid lumen 703 where temperature can be controlled and heat transfer occurs. Temperature is regulated by controlling the circulation of the heat transfer medium through the heat exchanging apparatus 798.

A guidewire lumen 708 is also provided to facilitate the insertion of a steerable guidewire and is sized and configured to reside in the wall of the outer tubular member 702. In alternative embodiments, the guidewire lumen 708 may be incorporated into one of the other lumens to create a more compact design or alternatively a fixed guidewire may be attached to the distal end of the catheter shaft 701, as is well known in the art. Furthermore, the guidewire lumen 708 can also serve as an instrument lumen for the insertion of other medical devices or microcatheters such as carotid stent catheters, aneurysm clip catheters, dilation catheters, diagnostic catheters, coil delivery catheters or occlusion catheters. The catheters can access the patient's vasculature through perfusion ports 709 or a specific access port sized and configured along the length of the catheter shaft.

The innermost tubular member 706 may be made from any of the materials described in connection with the previous embodiments, and in a preferred embodiment, stainless steel hypotube is used. The hypotube should be sufficiently rigid to sustain the high pressures of compressed gas or liquid, yet flexible enough to enable navigation through a patient's vasculature. With the aforementioned requirements in mind, the hypotube should have a wall thickness of approximately 0.001" to approximately 0.005", a diameter preferably of approximately 0.005" to approximately 0.100", more preferably approximately 0.020" to approximately 0.050". The first tubular member 706 has an expansion orifice 718 proximate its distal end. Heat exchanging medium is delivered through the lumen 707 and in the case of a compressed refrigerant, is allowed to expand through the expansion orifice into the return lumen(s) 705, facilitating heat along the length of the heat exchanging apparatus 798. Heat transfer can be accomplished through counterflow or alternatively by parallel flow.

The distal end of the inner tubular member 706 can also be configured to have a Joule-Thomson valve and the second tubular member can be configured with a heat transfer bellows element or a series of corrugations extending along the length. When cold or warm water is used, a closed system can be used by maintaining a higher pressure on the input of the inner tubular member 706 and a lower pressure on the output of the second tubular member 704 to create the desired heat transfer system.

The second tubular member 704 can be formed from a variety of materials, as discussed above, and in a preferred embodiment a high thermally conductive metal is used to enhance optimum heat transfer between the surface of the second inner tube 704 and fluid communicating within the fluid lumen 703. Examples of materials having high thermal conductivity include copper, gold, nitinol, platinum iridium and stainless steel. Furthermore, the second tubular member 704 may be constructed to have fins or other means for enhancing the surface area and corresponding heat transfer ability of the second tubular member 704. For example, in one preferred embodiment the tubular member 704 may be comprised of a substantially cylindrical tube having a plurality of substantially parallel longitudinal corrugations defining a plurality of exterior fluid flow channels and interior return channels for better heat exchange.

The catheter shaft 701 may be gradually tapering and formed from separate tubing pieces, which have the desired lumen configuration or alternatively may be attached end to end and bonded together by methods such as heat welding or adhesive bonding. The use of UV adhesive bonding and shrink tubing with heat application may be incorporated to ensure that assembled pieces are sealed fluid tight. Alternatively, the catheter shaft 701 may be fabricated by dipping or by composite construction techniques and joined together or the entire catheter shaft 701 may be fabricated integrally by known extrusion techniques. Furthermore, the use of tapered mandrels and a heat source can be used to neck down the outer diameter of the catheter shaft. In alternative embodiments, where it is desirable to have a catheter shaft with one continuous outer diameter, a single piece of tubing can be extruded and necked down to the proper dimensions.

The catheter shaft 701 should be of sufficient length to reach from an external location residing outside the body of a patient to a distant location residing within the internal lumen of the aorta proximate the arch vessels. With the aforementioned length requirements in mind, the overall size of the catheter 700 is preferably approximately 30 to 160 cm, more preferably approximately 50 cm to 120 cm, most preferably approximately 60 to 110 cm in length. The total outside diameter of the catheter shaft 701 should be of minimal size but of sufficient internal diameter to be able to provide adequate fluid flow as well as adequate heat transfer ability within the catheter shaft. Preferably the catheter 700 should be able to communicate fluid flow rates of approximately 0.10 L/min to 4 L/min, more preferably approximately 1 L/min to 2 L/min. With the aforementioned diameter requirements in mind the outside diameter of the catheter shaft 701 is preferably approximately 2 French to 24 French, more preferably approximately 4 French to 18 French, most preferably approximately 6 French to 14 French. In addition, the entire length of the outermost tubular member 702 may be dipped, coated or integrally constructed to have a thermal insulation to decrease thermal conductivity between the catheter 701 and the fluid residing in the vessel of the patient. Alternatively, only part of the catheter shaft 701 may be constructed to have thermal insulation.

Referring back to FIG. 18, the catheter 700 has a series of connectors/fittings attached to the proximal end of the catheter shaft 701 that serve a multitude of functions. A first tube fitting 770 is connected by known means to the output of a temperature regulation assembly 760 for delivering the heat exchange material to the delivery lumen 707 of the catheter 700. In one illustrative embodiment a compressed refrigerant such as liquid nitrogen or nitrous oxide is used to deliver the heat exchange material to the delivery lumen 707. In another illustrative embodiment, cold water is used. A second tube fitting 780 is connected by known means to the input of the temperature regulation assembly 760 to provide a return for the heat exchange material to the temperature regulation assembly 760. In alternative embodiments, the return lumen may open to atmosphere or to a separate holding chamber, rather than being recirculated through the temperature regulation assembly 760.

A fluid transport system 750 has an input(s) 752 and an output(s) 751 in fluid communication with the fluid lumen 703 of the catheter 700. In this illustrative embodiment, an internal pump 753 is used. The fluid transportation system has a luer connector 754 for delivering pharmacological agents or fluid sampling and a Touhy-Borst fitting 756, hemostasis valve or other suitable fitting for insertion of a guidewire or other medical instrument, as described in any of the previously described embodiments. Alternatively, in another illustrative embodiment, external pump(s) can be used and blood can be withdrawn through the same vessel that the catheter 700 is introduced or through any other peripheral artery and connected to the fluid lumen 703 through tubing connectors.

While the particular invention as herein shown and disclosed is capable of solving the problems stated herein, it is to be understood that any combination of the previously described embodiments can be used in combination with one another and the descriptions are intended to describe illustrative embodiments. The present invention is capable of cooling or warming tissue and organs and can be introduced into any vessel including, the venous system or the arterial system.

We claim:

1. A catheter comprising:
   a catheter shaft;
   a heat exchanging apparatus extending at least in part within said catheter shaft;
   an expandable membrane coupled to said catheter shaft;
   wherein said heat exchanging apparatus is further comprised of:
     a delivery lumen adapted to communicate a heat exchanging medium at least in part through said catheter shaft; and
     a return lumen in communication with said delivery lumen for communicating said heat exchanging medium at least in part through said catheter shaft.

2. The catheter of claim 1, wherein said delivery lumen and said return lumen extend in a substantially coaxial relationship.

3. The catheter of claim 2, wherein said expandable membrane further comprises at least one expandable rib.

4. The catheter of claim 3, wherein said expandable membrane is in fluid communication with said heat exchanging medium.

5. The catheter of claim 1, further comprising:
   an occluding member coupled to said catheter shaft.

6. A catheter comprising:
   a catheter shaft;
   a heat exchanging apparatus extending at least in part within said catheter shaft, said heat exchanging apparatus having a heat transfer interface adapted to alter the temperature of a fluid communicated through the catheter shaft; and
   a fluid lumen adapted to communicate said fluid through said catheter shaft such that said fluid is in a heat transfer relationship with said heat transfer interface, said fluid lumen in fluid communication with an internal pump.

7. The catheter of claim 6, wherein said heat exchanging apparatus extends through said internal pump.

8. The catheter of claim 6, wherein said heat exchanging apparatus does not extend through said internal pump.

9. The catheter of claim 6, wherein said heat exchanging apparatus extends at least in part in a parallel relationship with said fluid lumen.

10. The catheter of claim 6, further comprising:
    a guidewire lumen sized and configured for the introduction of a steerable guidewire.

11. The catheter of claim 10, wherein said guidewire lumen is sized and configured for the insertion of a medical device selected from the group consisting of an angioplasty catheter, a stent placement catheter, an atherectomy catheter, a valvuloplasty catheter, an electrophysiology catheter, a transmyocardial revascularization catheter, a patent ductus arteriosus closure catheter, a septal defect repair catheter, an intravascular ultrasonic imaging catheter, a laser angioplasty catheter, a laser ablation catheter, a coil delivery catheter, an embolic delivery catheter, a filter catheter, a carotid stent catheter, a carotid endarterectomy catheter, a tPA drug delivery catheter and a clot dissolving catheter.

12. A catheter comprising:
    a catheter shaft;
    a heat exchanging apparatus extending at least in part within said catheter shaft, said heat exchanging apparatus having a heat transfer interface adapted to alter the temperature of a fluid communicated through the catheter shaft;
    a fluid lumen adapted to communicate said fluid through said catheter shaft such that said fluid is in a heat transfer relationship with said heat transfer interface, said fluid lumen defined by the internal lumen of said catheter shaft;
    an expandable membrane coupled to said catheter shaft:
    a perfusion port in fluid communication with said fluid lumen; and
    a pump adapted to communicate said fluid to said fluid lumen such that said fluid is perfused from said perfusion port.

13. The catheter of claim 12, wherein said pump is an internal pump.

14. The catheter of claim 12, wherein said pump is an external pump.

15. A method of selectively altering the temperature of tissue comprising the steps of:
    introducing a catheter having a catheter shaft and a heat exchanging apparatus extending at least in part within said catheter shaft into the vasculature of a patient, said heat exchanging apparatus having a heat transfer interface adapted to alter the temperature of a fluid communicated through the catheter shaft;
    communicating said fluid through said catheter shaft; and
    reducing the temperature of said heat exchanging apparatus; and
    pumping blood over said heat exchanging apparatus.

16. The method of selectively altering the temperature of tissue of claim 15, further comprising the step of:
    inserting a medical device through said catheter shaft.

17. The method of selectively altering the temperature of tissue of claim 15, further comprising the step of cooling the brain with said blood.

18. The method of selectively altering the temperature of tissue of claim 15, further comprising the step of perfusing the corporeal circulation with a beating heart.

19. The method of selectively altering the temperature of tissue of claim 15, further comprising the steps of:
expanding an expandable membrane in the aorta of a patient;
flowing said fluid over said heat exchanging apparatus to cool said fluid;
perfusing the cerebral circulation with said fluid; and
perfusing the corporeal circulation through a heart.

20. The method of selectively altering the temperature of tissue of claim 19, wherein the step of perfusing the corporeal circulation is carried out by:
perfusing the corporeal circulation through a beating heart.

21. The method of selectively altering the temperature of tissue of claim 19, wherein the step of perfusing the cerebral circulation is carried out by:
perfusing with an internal pump.

22. The method of selectively altering the temperature of tissue of claim 19, wherein the step of perfusing the cerebral circulation is carried out by:
perfusing with an external pump.

23. A catheter comprising:
a catheter shaft;
a heat exchanging apparatus extending at least in part within said catheter shaft, said heat exchanging apparatus is further comprised of:
a delivery lumen adapted to communicate a heat exchanging medium at least in part through said catheter shaft; and
a return lumen in communication with said delivery lumen for communicating said heat exchanging medium at least in part through said catheter shaft; and
an occluding member coupled to said catheter shaft.

24. A catheter comprising:
a heat exchanging apparatus comprising:
a pair of coaxial tubes for carrying a heat exchanging medium, said pair of coaxial tubes defining a delivery path for the heat exchanging medium and a return path for the heat exchanging medium, where said delivery path and said return path are separated by a wall of one of said tubes and a pressure of the heat exchanging medium is greater in the delivery path than in the return path, and
a plurality of expansion orifices located on the wall, where said heat exchanging medium expands through said expansion orifices from said delivery path to said return path; and
a lumen in adjacent to said heat exchanging apparatus for communicating a fluid therethrough, a temperature of said fluid moderated by the lumen's proximity with the heat exchanging apparatus.

25. The catheter of claim 24 wherein the heat exchanging medium comprises nitrous oxide.

26. The catheter of claim 24 wherein a spacing between the expansion orifices is selected to allow for uniform cooling along a length of the return path.

27. A catheter comprising:
a heat exchanging apparatus comprising:
a pair of coaxial tubes for carrying a heat exchanging medium, said pair of coaxial tubes defining a delivery path for the heat exchanging medium and a return path for the heat exchanging medium, where said delivery path and said return path are separated by a wall of one of said tubes and said wall included a plurality of longitudinal corrugations defining a plurality of exterior fluid flow channels and interior fluid flow channels; and
a lumen in adjacent to said heat exchanging apparatus for communicating a fluid therethrough, a temperature of said fluid moderated by the lumen's proximity with the heat exchanging apparatus.

28. A method for rapidly cooling a brain comprising:
providing a catheter with blood perfusion ports;
inserting the catheter into operative position where the perfusion ports are adjacent arch vessels of the heart;
passing blood into the catheter;
cooling the blood within the catheter; and
delivering the cooled blood to the cerebral circulation through the perfusion ports.

29. A catheter comprising:
a catheter shaft;
a heat exchanging apparatus extending at least in part within said catheter shaft; said heat exchanging apparatus having a heat transfer interface adapted to alter the temperature of a fluid communicated through the catheter shaft;
a fluid lumen adapted to communicate said fluid through said catheter shaft such that said fluid is in a heat transfer relationship with said heat transfer interface, said fluid lumen defined by the internal lumen of said catheter shaft; and
an expandable membrane coupled to said catheter shaft wherein said fluid communicated through the catheter shaft is introduced into the expandable member the expandable membrane comprising a flow divider to thermally insulate a first surface while fluid alters the temperature of a second surface.

30. A catheter comprising:
a catheter shaft;
a heat exchanging apparatus extending at least in part within said catheter shaft, said heat exchanging apparatus having a heat transfer interface adapted to alter the temperature of a fluid communicated through the catheter shaft;
an expandable membrane coupled to said catheter shaft, said expandable membrane further comprising at least one expandable rib.

31. The catheter of claim 30, wherein said expandable membrane is in fluid communication with said heat exchanging medium.

* * * * *